(12) United States Patent
Erickson et al.

(10) Patent No.: US 9,533,164 B2
(45) Date of Patent: Jan. 3, 2017

(54) METHOD FOR PROVIDING MULTIPLE VOLTAGE LEVELS DURING PULSE GENERATION AND IMPLANTABLE PULSE GENERATING EMPLOYING THE SAME

(75) Inventors: John H. Erickson, Plano, TX (US); Robert L. McCormick, Frisco, TX (US); Benjamin A. Tranchina, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 2541 days.

(21) Appl. No.: 12/245,208

(22) Filed: Oct. 3, 2008

(65) Prior Publication Data
US 2009/0048643 A1    Feb. 19, 2009

Related U.S. Application Data

(63) Continuation-in-part of application No. 11/420,670, filed on May 26, 2006, now Pat. No. 7,571,007, and
(Continued)

(51) Int. Cl.
*A61N 1/378* (2006.01)

(52) U.S. Cl.
CPC .............. *A61N 1/378* (2013.01); *A61N 1/3787* (2013.01)

(58) Field of Classification Search
CPC ............................. A61N 1/378; A61N 1/3787
(Continued)

(56) References Cited

U.S. PATENT DOCUMENTS 3,893,463 A    7/1975  Williams
3,911,930 A    10/1975  Hagfors et al.
(Continued)

FOREIGN PATENT DOCUMENTS

EP    0734740    10/1996
JP    03163613    7/1991
(Continued)

OTHER PUBLICATIONS

International Search Report issued for PCT/US2005/012253 dated Aug. 5, 2005.
(Continued)

*Primary Examiner* — Catherine Voorhees

(57) ABSTRACT

In one embodiment, a method of operating an implantable pulse generator comprises: providing power to a voltage converter at a first voltage level; outputting a second voltage level by the voltage converter, the second voltage level being a variable voltage level that is controlled by a control signal provided to the voltage converter, the second voltage level being provided to pulse generating circuitry of the implantable pulse generator, the second voltage level being selectable from a plurality of voltages including non-integer multiples of the first voltage level; generating pulses by the pulse generating circuitry, the pulse generating circuitry including current control circuitry for controlling the pulses to cause the pulses to provide substantially constant current to tissue of the patient; and applying at least two different control signals to the voltage converter during individual pulses to provide successively increasing voltages to the pulse generating circuitry during a respective pulse.

20 Claims, 11 Drawing Sheets

Related U.S. Application Data a continuation-in-part of application No. 11/105,191, filed on Apr. 12, 2005, now Pat. No. 7,450,987, which is a continuation-in-part of application No. 11/105,186, filed on Apr. 12, 2005, now abandoned, which is a continuation-in-part of application No. 11/105,188, filed on Apr. 12, 2005, now abandoned, which is a continuation-in-part of application No. 11/105,332, filed on Apr. 12, 2005, now Pat. No. 7,180,760, which is a continuation-in-part of application No. 11/105,190, filed on Apr. 12, 2005, now abandoned.

(60) Provisional application No. 60/685,036, filed on May 26, 2005, provisional application No. 60/561,437, filed on Apr. 12, 2004.

(58) Field of Classification Search
USPC .......................................... 607/9, 46, 59, 64
See application file for complete search history.

(56) References Cited

U.S. PATENT DOCUMENTS

| | | | |
|---|---|---|---|
| 4,050,004 A | | 9/1977 | Greatbatch |
| 4,062,365 A | | 12/1977 | Kameny |
| RE32,091 E | * | 3/1986 | Stanton ........................ 607/48 |
| 4,578,772 A | | 3/1986 | Fujii |
| 4,702,254 A | | 10/1987 | Zabara et al. |
| 5,052,391 A | | 10/1991 | Silberstone et al. |
| 5,058,582 A | | 10/1991 | Thaler et al. |
| 5,063,929 A | * | 11/1991 | Bartelt et al. .................. 607/63 |
| 5,154,172 A | | 10/1992 | Terry et al. |
| 5,167,229 A | | 12/1992 | Peckham et al. |
| 5,179,950 A | | 1/1993 | Stanislow |
| 5,222,494 A | | 6/1993 | Baker, Jr. |
| 5,350,407 A | | 9/1994 | Mcclure et al. |
| 5,350,412 A | | 9/1994 | Hoegnelid et al. |
| 5,370,666 A | | 12/1994 | Lindberg et al. |
| 5,411,537 A | | 5/1995 | Munshi et al. |
| 5,414,614 A | | 5/1995 | Fette et al. |
| 5,548,238 A | | 8/1996 | Zhang et al. |
| 5,593,427 A | | 1/1997 | Gliner et al. |
| 5,601,608 A | | 2/1997 | Mouchawar |
| 5,680,300 A | | 10/1997 | Szepesi et al. |
| 5,683,422 A | | 11/1997 | Rise et al. |
| 5,767,735 A | | 6/1998 | Javanifard et al. |
| 5,846,264 A | | 12/1998 | Andersson et al. |
| 5,859,527 A | | 1/1999 | Cook |
| 5,903,136 A | | 5/1999 | Takahashi et al. |
| 5,948,004 A | | 9/1999 | Weijand et al. |
| 5,964,787 A | | 10/1999 | Kerver et al. |
| 5,969,508 A | | 10/1999 | Patino et al. |
| 5,999,040 A | | 12/1999 | Do et al. |
| 6,021,056 A | | 2/2000 | Forbes et al. |
| 6,169,673 B1 | | 1/2001 | McIntyre et al. |
| 6,198,645 B1 | | 3/2001 | Kotowski et al. |
| 6,233,186 B1 | | 5/2001 | Tonda |
| 6,609,031 B1 | | 8/2003 | Law et al. |
| 6,657,875 B1 | | 12/2003 | Zeng et al. |
| 6,895,278 B1 | | 5/2005 | Gordon |
| 6,934,584 B1 | * | 8/2005 | Wong et al. ..................... 607/9 |
| 6,956,355 B2 | | 10/2005 | Vaillancourt et al. |
| 7,123,958 B1 | | 10/2006 | Wong |
| 7,127,288 B2 | | 10/2006 | Sturman et al. |
| 7,136,701 B2 | | 11/2006 | Greatbatch et al. |
| 7,174,207 B2 | | 2/2007 | Dodd et al. |
| 7,177,690 B2 | | 2/2007 | Woods et al. |
| 7,177,703 B2 | | 2/2007 | Boveja et al. |
| 7,221,980 B2 | | 5/2007 | Kotlik et al. |
| 7,295,878 B1 | | 11/2007 | Meadows et al. |
| 7,805,189 B2 | | 9/2010 | Stein et al. |
| 2002/0068957 A1 | | 6/2002 | Wolf et al. |
| 2002/0077572 A1 | | 6/2002 | Fang et al. |
| 2002/0101744 A1 | | 8/2002 | DeMone |
| 2003/0006835 A1 | | 1/2003 | Lee et al. |
| 2003/0038637 A1 | | 2/2003 | Bertness et al. |
| 2003/0052729 A1 | | 3/2003 | Hsu et al. |
| 2003/0058666 A1 | | 3/2003 | Myono |
| 2004/0167407 A1 | | 8/2004 | Roberts |
| 2004/0210270 A1 | * | 10/2004 | Erickson ..................... 607/46 |
| 2004/0215260 A1 | | 10/2004 | Vonk et al. |
| 2005/0245977 A1 | * | 11/2005 | Varrichio et al. ............ 607/11 |
| 2006/0004423 A1 | * | 1/2006 | Boveja et al. ................ 607/46 |
| 2006/0259098 A1 | * | 11/2006 | Erickson ..................... 607/61 |

FOREIGN PATENT DOCUMENTS

| | | |
|---|---|---|
| WO | WO 8707511 | 12/1987 |
| WO | WO 9604957 | 2/1996 |
| WO | WO 9962594 | 12/1999 |

OTHER PUBLICATIONS

International Search Report issued for PCT/US2005/012477 dated Aug. 4, 2005.

International Search Report issued for PCT/US2005/012480 dated Aug. 11, 2005.

International Search Report issued for PCT/US2005/012361 dated Aug. 3, 2005.

International Search Report issued for PCT/US2005/012254 dated Jul. 19, 2005.

International Search Report issued for PCT/US2006/020562 dated Dec. 27, 2006.

* cited by examiner

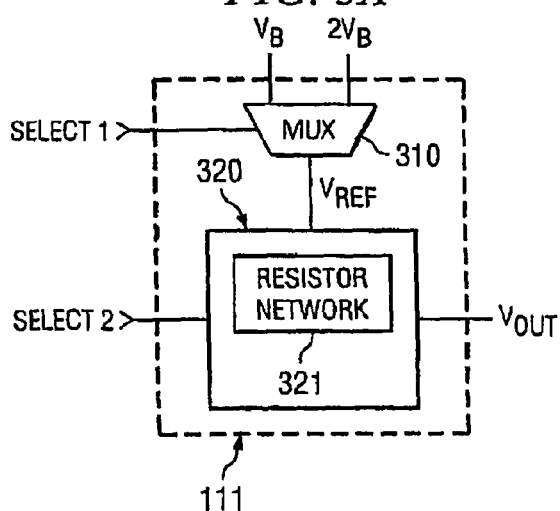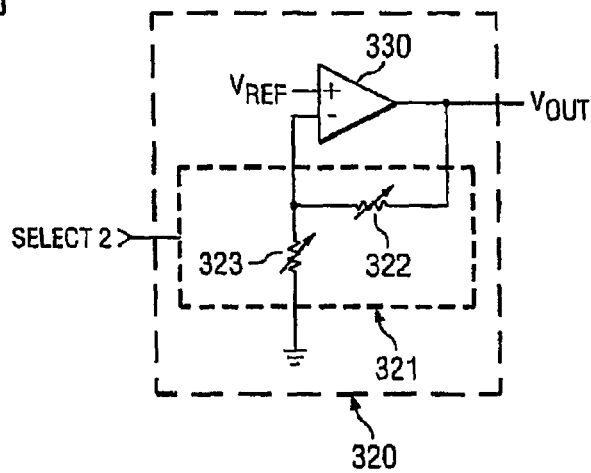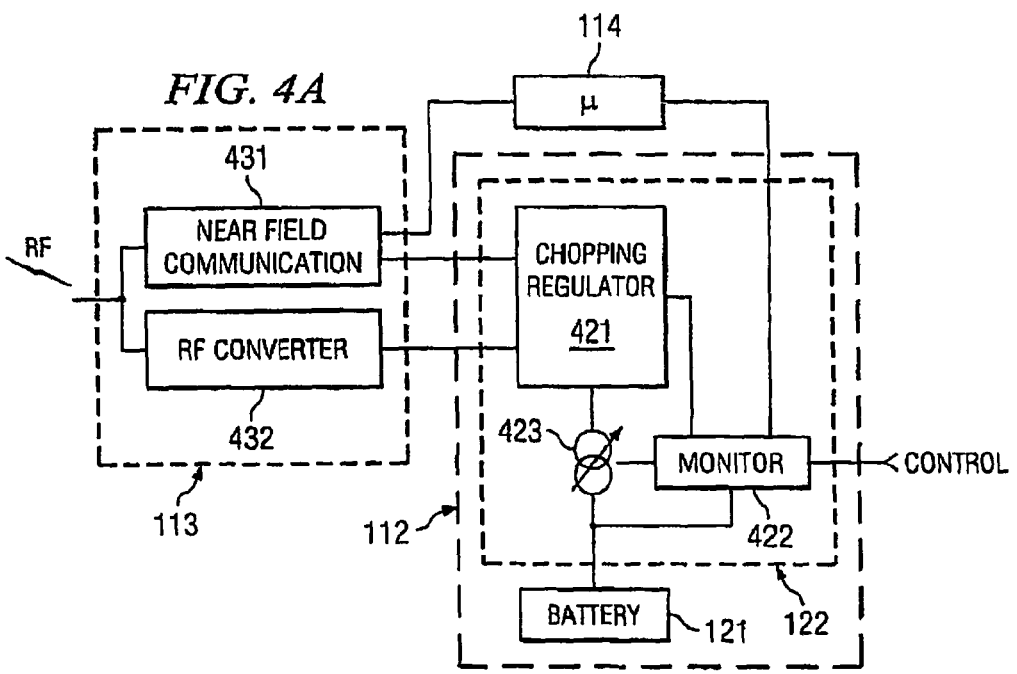

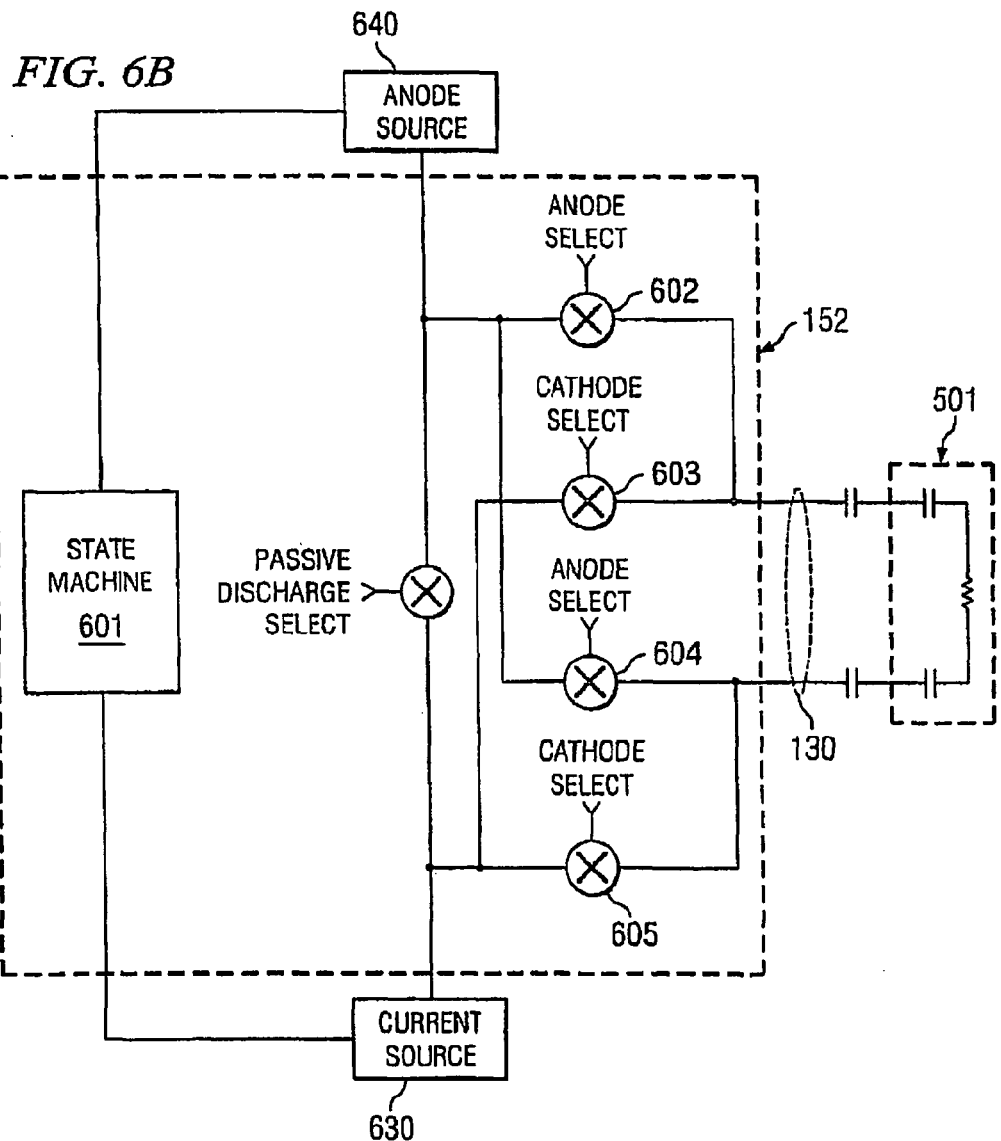

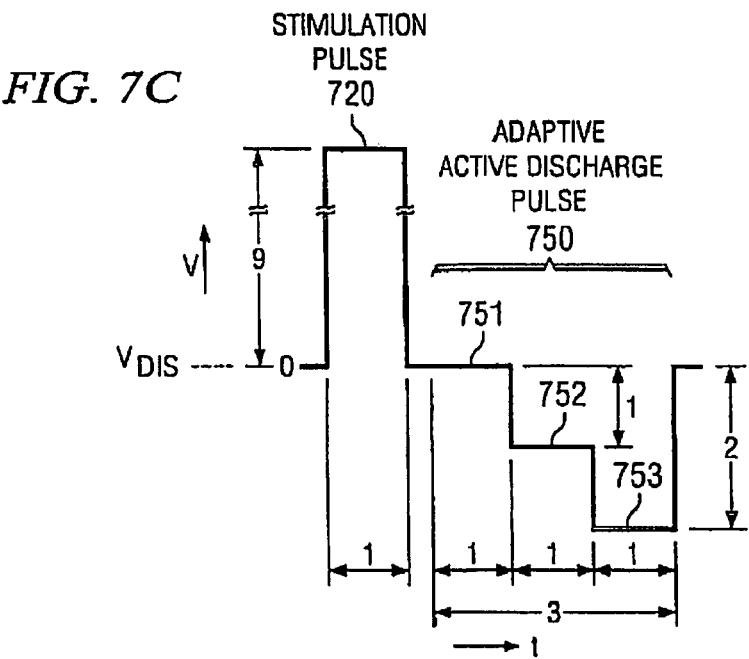
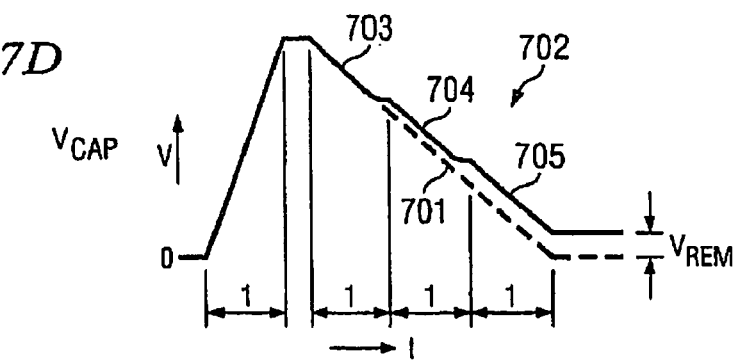

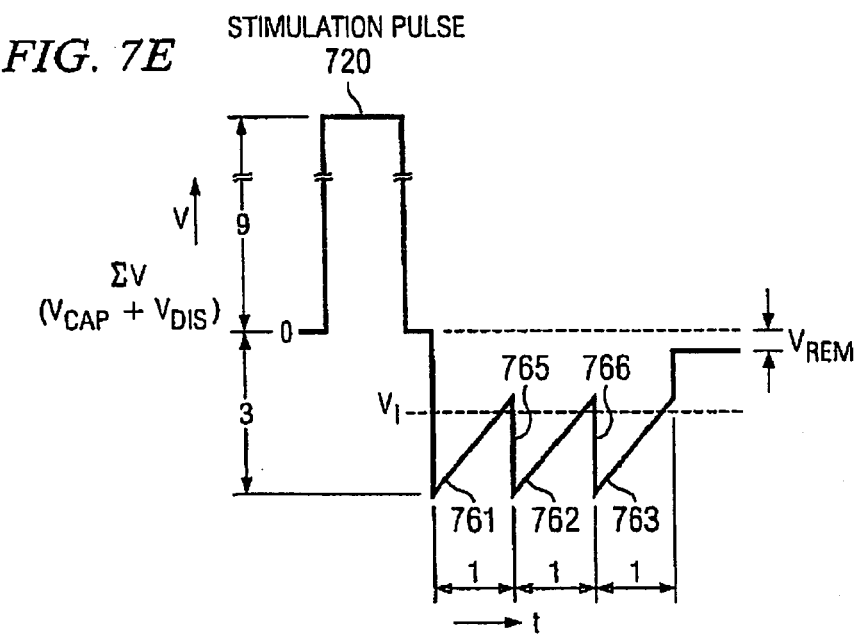
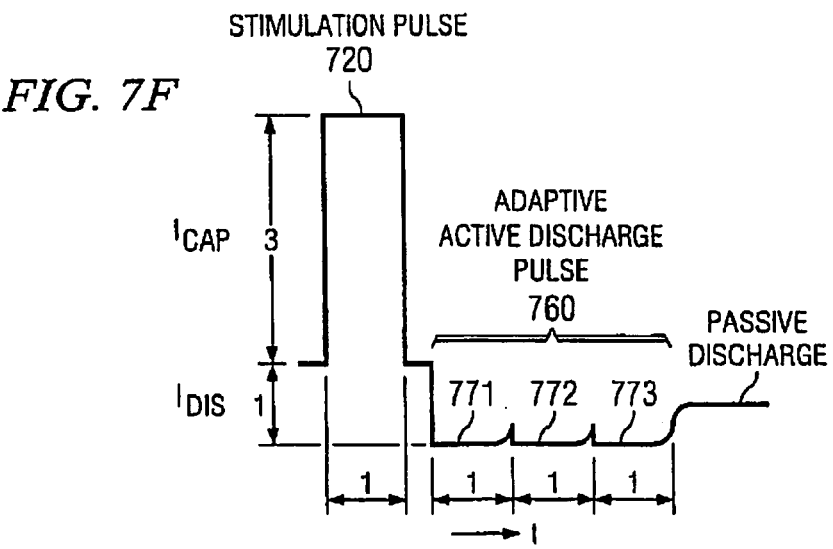

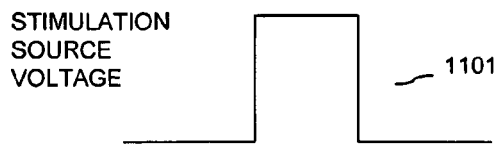
FIG. 11A
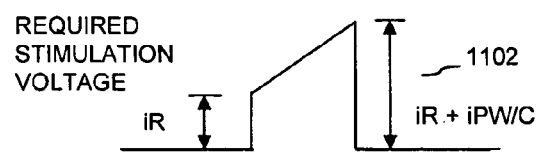
FIG. 11B
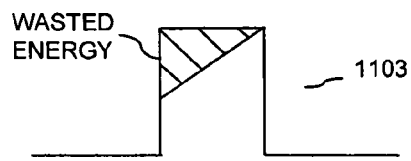
FIG. 11C
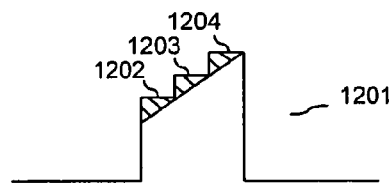
FIG. 12
| A1 | V1 | V1 | V1 |
| --- | --- | --- | --- |
| A2 | V1 | V1 | V2 |
| A3 | V1 | V2 | V3 |
| A4 | V2 | V3 | V4 |
FIG. 13

METHOD FOR PROVIDING MULTIPLE VOLTAGE LEVELS DURING PULSE GENERATION AND IMPLANTABLE PULSE GENERATING EMPLOYING THE SAME

CROSS-REFERENCE TO RELATED APPLICATIONS

This application is a continuation-in-part of U.S. patent application Ser. No. 11/420,670, filed May 26, 2006, now U.S. Pat. No. 7,571,007, which claims the benefit of U.S. Provisional Application Ser. No. 60/685,036, entitled "SYSTEM AND METHOD FOR USE IN PULSE GENERATION," filed May 26, 2005 and which is a continuation-in-part of each of the following applications: (i) U.S. patent application Ser. No. 11/105,191, filed Apr. 12, 2005, now U.S. Pat. No. 7,450,987, entitled "SYSTEMS AND METHODS FOR PRECHARGING CIRCUITRY FOR PULSE GENERATION," (which claims the benefit of U.S. Provisional Application Ser. No. 60/561,437, filed Apr. 12, 2004); (ii) U.S. patent application Ser. No. 11/105,186, filed Apr. 12, 2005, abandoned, entitled "SYSTEMS AND METHODS FOR PROVIDING AMPLITUDE SELECTION FOR PULSE GENERATION," (which claims the benefit of U.S. Provisional Application No. 60/561,437, filed Apr. 12, 2004); (iii) U.S. patent application Ser. No. 11/105,188, abandoned, entitled "ACTIVE DISCHARGE SYSTEMS AND METHODS," filed Apr. 12, 2005 (which claims the benefit of U.S. Provisional Application No. 60/561,437, filed Apr. 12, 2004); (iv) U.S. patent application Ser. No. 11/105,332, now U.S. Pat. No. 7,180,760, entitled "FRACTIONAL VOLTAGE CONVERTER," filed Apr. 12, 2005 (which claims the benefit of U.S. Provisional Application No. 60/561,437); and (v) U.S. patent application Ser. No. 11/105,190, abandoned, entitled "VOLTAGE LIMITED SYSTEMS AND METHODS," filed Apr. 12, 2005 (which claims the benefit of U.S. Provisional Application No. 60/561,437, filed Apr. 12, 2004), all of which are incorporated herein by reference.

TECHNICAL FIELD

The present application relates generally to implantable pulse generators and circuitry useful therewith.

BACKGROUND

The use of electronic stimulation systems to control pain or other indications, or to otherwise provide therapy, by nerve or muscle stimulation has been in use for a number of years. For example, spinal cord stimulation (SCS) is a technique that has been used for pain management since the 1960s. Of course, stimulation systems may be used in stimulating areas other than the spinal cord, such as for deep brain stimulation, muscle stimulation, etcetera.

Stimulation systems often comprise a pulse generator coupled to one or more percutaneous leads having a plurality of electrodes disposed in an area in which neurostimulation is desired. Alternatively, stimulation systems may comprise a micro-stimulation systems in which a small implantable housing having electrodes thereon includes a pulse generator, wherein the entire micro-stimulation system is disposed in an area in which neurostimulation is desired. Of course, all or a portion of a stimulation system need not be implanted into a body to provide a desired therapy.

A stimulation system pulse generator may be provided in various configurations, such as a totally implanted pulse generator (IPG) or a radio frequency (RF) system. A typical IPG configuration comprises a surgically implanted, internally-powered pulse generator and multi-electrode lead. A typical RF system configuration comprises a surgically implanted, passive receiver and a transmitter which is worn externally. In operation, the transmitter communicates, through an RF signal, to the implanted receiver to provide stimulation energy and control.

Electrodes used with the foregoing pulse generators deliver a particularized electric field to a specific region of the spinal cord or surrounding tissue. Applying such an electric field across one or more nerve bundles and/or nerve roots, if properly directed and produced at the necessary levels, can "mask" certain forms of chronic pain. Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the electric pulse waveform (collectively "stimulation setting"). The waveform properties generally include a stimulation frequency, a stimulation pulse width, and phase information.

Implantation of all or a portion of a stimulation system, e.g., a stimulation system including a fully implanted IPG or a RF system receiver/transmitter, necessarily requires a neurostimulation patient to undergo an implantation surgery. Additionally, routing a lead subdermally between an implanted pulse generator and the tissue area to be stimulated typically requires a relatively invasive procedure, such as a tunneling procedure. Likewise, explanting all or a portion of a stimulation system requires a neurostimulation patient to again undergo the trauma of surgery.

SUMMARY

Some embodiments are directed to systems and methods which are adapted to provide reliable and long lived operation of a pulse generator through use of battery charge control circuitry, fractional voltage conversion circuitry, efficient pulse generation/delivery techniques (including active discharge, pulse ramping, pulse wave shaping, etcetera), and/or efficient clocking techniques. Systems and methods of selected embodiments provide long lived operation of a host system, such as a therapeutic stimulation pulse generation system, by optimizing the use of available energy while providing desired operation with respect to a host system. Accordingly, some embodiments are particularly well suited for use in systems which operate from battery, or otherwise limited, power, such as implantable stimulation pulse generation systems.

The foregoing has outlined rather broadly the features and technical advantages of some embodiments in order that the detailed description of the invention that follows may be better understood. Additional features and advantages will be described hereinafter which form the subject of the claims of the invention. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWING

FIGS. 3A and 3B show additional detail with respect to a voltage regulator of the system of FIG. 1 according to some embodiments.

FIG. 4A shows additional detail with respect to a receiver and power supply of the system of FIG. 1 according to some embodiments.

FIGS. 6A and 6B show additional detail with respect to a voltage/current control circuit of the system of FIG. 1 according to some embodiments.

FIGS. 7A-7F show diagrams of current and voltage verses time for active discharge techniques of some embodiments.

FIGS. 11A-11C depict a graph of a constant voltage level selected for a stimulation pulse, a graph of the instantaneous voltage required for a constant current stimulation pulse, and a graph of wasted energy when a constant voltage level is selected for a constant current stimulation pulse.

FIG. 12 depicts a voltage profile of a stimulation pulse according to one representative embodiment.

FIG. 13 depicts a table defining voltage profiles that may be used to generate stimulation pulses according to one representative embodiment.

DETAILED DESCRIPTION

Some embodiments are described herein with respect to an implantable pulse generator (IPG) for generating electrical stimulation for application to a desired area of a body, such as a spinal cord stimulation (SCS) system. The circuitry and methods of operation disclosed herein are not limited to an implantable pulse generator for use in an spinal cord stimulation system, but have broad applicability, including but not limited to different types of implantable devices such as spinal and neural stimulators and sensors, deep brain stimulators, cochlear stimulators, drug delivery systems, muscle stimulators, tissue stimulators, cardiac pacemaker, gastric stimulator, and the like, including sensors and sensing systems. Moreover, the circuitry and methods of operation disclosed herein are not limited to use with respect to an IPG or any particular form of IPG For example, some embodiments may be implemented with respect to a fully implantable pulse generator, a radio frequency pulse generator, an external pulse generator, a micro-implantable pulse generator, etcetera.

Figure 1:
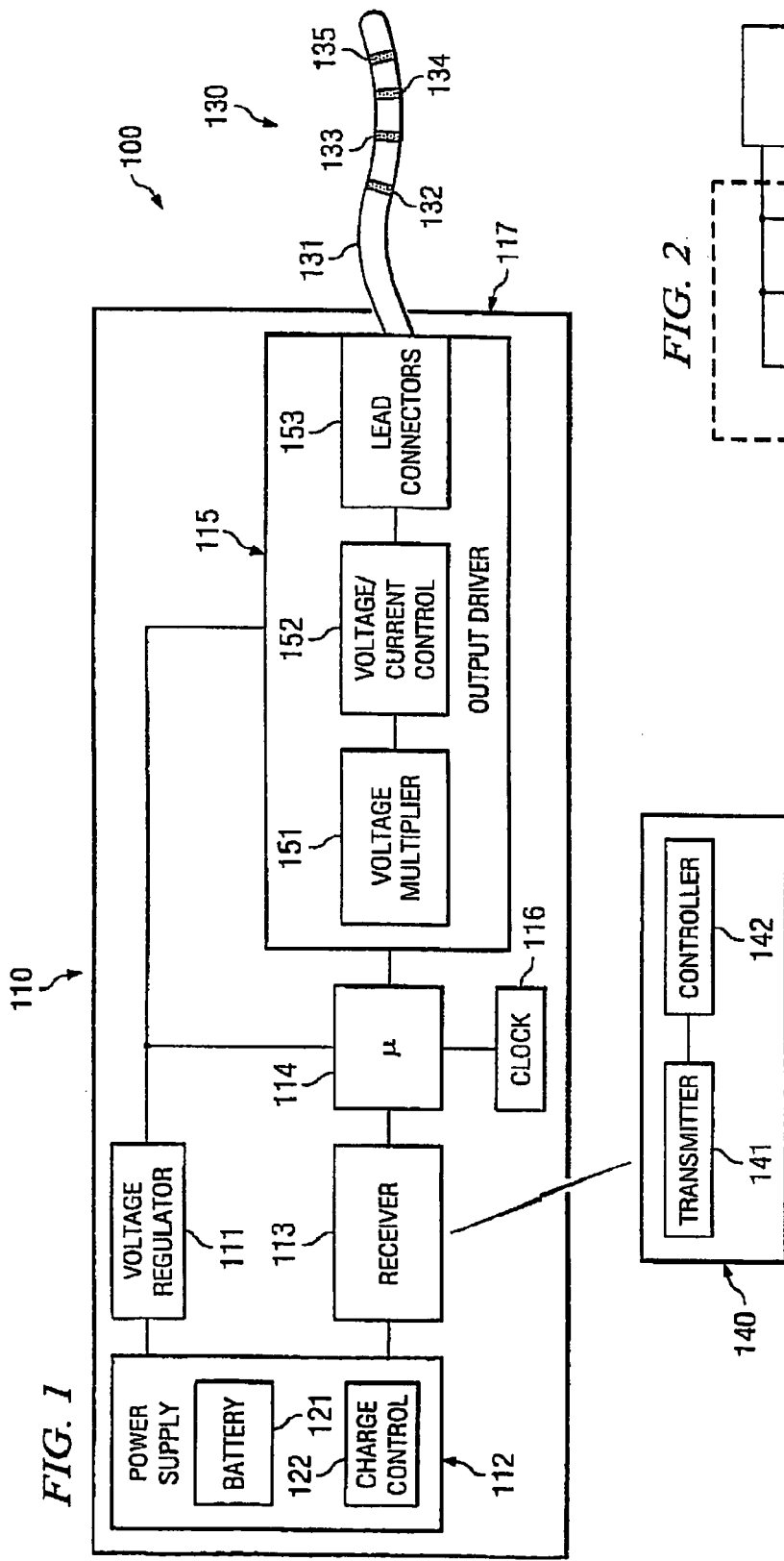
FIG. 1 shows a high level functional block diagram of a stimulation system implementing some embodiments.

Directing attention to FIG. 1, stimulation system 100 is adapted according to an embodiment and is shown in a high level functional block diagram. In operation, stimulation system 100 generates and applies a stimulus to tissue or a certain location of a body. Stimulation system 100 of the illustrated embodiment includes a generator portion, shown as implantable pulse generator (IPG) 110, providing a stimulation or energy source, stimulation portion, shown as lead 130, for application of the stimulus pulse(s), and an optional external controller, shown as programmer/controller 140, to program and/or control implantable pulse generator 110 via a wireless communications link. IPG 110 may be implanted within a living body (not shown) for providing electrical stimulation from IPG 110 to a selected area of the body via lead 130, perhaps under control of external programmer/controller 140. It should be appreciated that, although lead 130 is illustrated to provide a stimulation portion of stimulation system 100 configured provide stimulation remotely with respect to the generator portion of stimulation system 100, a lead as described herein is intended to encompass a variety of stimulation portion configurations. For example, lead 130 may comprise a microstimulator electrode disposed adjacent to a generator portion. Furthermore, a lead configuration may include more (e.g., 8, 16, 32, etcetera) or fewer (e.g., 1, 2, etcetera) electrodes than those represented in the illustrations.

IPG 110 may comprise a self-contained implantable pulse generator having an implanted power source such as a long-lasting or rechargeable battery. Alternatively, IPG 110 may comprise an externally-powered implantable pulse generator receiving at least some of the required operating power from an external power transmitter, preferably in the form of a wireless signal, which may be radio frequency (RF), inductive, etc.

IPG 110 of the illustrated embodiment includes voltage regulator 111, power supply 112, receiver 113, microcontroller (or microprocessor) 114, output driver circuitry 115, and clock 116, as are described in further detail below. Power supply 112 provides a source of power, such as from battery 121 (battery 121 may comprise a non-rechargeable (e.g., single use) battery, a rechargeable battery, a capacitor, and/or like power sources), to other components of IPG 110, as may be regulated by voltage regulator 111. Charge control 122 of embodiments provides management with respect to battery 121. Receiver 113 of embodiments provides data communication between microcontroller 114 and controller 142 of external programmer/controller 140, via transmitter 141. It should be appreciated that although receiver 113 is shown as a receiver, a transmitter and/or transceiver may be provided in addition to or in the alternative to receiver 113, depending upon the communication links desired. Receiver 113 of embodiments, in addition to or in the alternative to providing data communication, provides a conduit for delivering energy to power supply 112, such as where RF or inductive recharging of battery 121 is implemented. Microcontroller 114 provides control with respect to the operation of IPG 110, such as in accordance with a program provided thereto by external programmer/controller 140. Output driver circuitry 115 generates and delivers pulses to selected ones of electrodes 132-135 under control of microcontroller 114. For example, voltage multiplier 151 and voltage/current control 152 may be controlled to deliver a constant current pulse of a desired magnitude, duration, and frequency to a load present with respect to particular ones of electrodes 132-135. Clock 116 preferably provides system timing information, such as may be used by microcontroller 114 in controlling system operation, as may be used by voltage multiplier 151 in generating a desired voltage, etcetera.

Lead 130 of the illustrated embodiment includes lead body 131, preferably incarcerating a plurality of internal conductors coupled to lead connectors (not shown) to interface with lead connectors 153 of IPG 110. Lead 130 further includes electrodes 132-135, which are preferably coupled to the aforementioned internal conductors. The internal conductors provide electrical connection from individual lead connectors to each of a corresponding one of electrodes 132-235. In the exemplary embodiment the lead 130 is generally configured to transmit one or more electrical signals from IPG 110 for application at, or proximate to, a spinal nerve or peripheral nerve, brain matter, muscle, or other tissue via electrodes 132-135. IPG 110 is capable of controlling the electrical signals by varying signal parameters such as intensity, duration and/or frequency in order to deliver a desired therapy or otherwise provide operation as described herein.

Although the embodiment illustrated in FIG. 1 includes 4 electrodes, it should be appreciated that any number of electrodes, and corresponding conductors, may be utilized according to some embodiments. Moreover, various types, configurations and shapes of electrodes (and lead connectors) may be used according to some embodiments. An optional lumen (not shown) may extend through the lead 130, such as for use in delivery of chemicals or drugs or to accept a stylet during placement of the lead within the body. Additionally or alternatively, the lead (stimulation portion) and IPG (generator portion) may comprise a unitary construction, such as that of a microstimulator configuration.

As mentioned above, programmer/controller 114 of embodiments provides data communication with IPG 110, such as to provide control (e.g., adjust stimulation settings), provide programming (e.g., alter the electrodes to which stimulation pulses are delivered), etcetera. Accordingly, programmer/controller 114 of the illustrated embodiment includes transmitter 141, for establishing a wireless link with IPG 110, and controller 142, to provide control with respect to programmer/controller 114 and IPG 110. Additionally or alternatively, programmer/controller 114 may provide power to IPG 110, such as via RF transmission by transmitter 141. Optionally, however, a separate power controller may be provided for charging the power source within IPG 110.

Additional detail with respect to pulse generation systems and the delivery of stimulation pulses may be found in U.S. Pat. No. 6,609,031, entitled "MULTIPROGRAMMABLE TISSUE STIMULATOR AND METHOD," the disclosure of which is hereby incorporated herein by reference. Similarly; additional detail with respect to pulse generation systems and the delivery of stimulation pulses may be found in the above referenced patent application entitled "MULTI-PROGRAMMABLE TRIAL STIMULATOR."

Having generally described stimulation system 100 above, the discussion which follows provides detail with respect to various functional aspects of stimulation system 100 according to some embodiments. Although the below embodiments are described with reference to stimulation system 100, and IPG 110 thereof, it should be appreciated that the inventive concepts described herein are not limited to application to the exemplary system, and may be used in a wide variety of medical devices.

Clock

Figure 2:
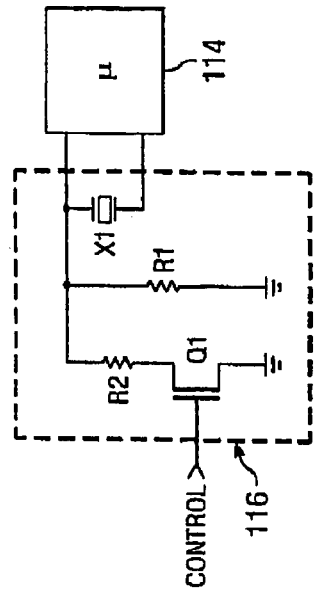
FIG. 2 shows additional detail with respect to a clock of the system of FIG. 1 according to some embodiments.

Directing attention to FIG. 2, detail with respect to an embodiment of clock 116 of FIG. 1 is shown. Clock signals used by IPG 110 of the illustrated embodiment are driven by crystal X1 and establish the rate at which operations are performed by components of IPG 110. For example, a rate at which instructions are processed by microcontroller 114 of embodiments are controlled by a clock signal provided thereto by clock 116. Likewise, a rate at which capacitors are charged and stacked for generating a desired voltage by voltage multiplier 151 of embodiments is controlled by a clock signal provided thereto by clock 116.

Various system parameters can define the clock speed needed or used in any particular configuration. For example, the desire to have control of pulse width to 10 microseconds can drive the system design to incorporate a clock providing a clock signal having a frequency of 100 kilohertz. However, many components may not be capable of reliable operation at or above particular clock frequencies. For example, microcontrollers, such as microcontroller 114, are often designed to operate at a standard clock crystal frequency (e.g., 32.768 kHz), although reliable operation may be provided at somewhat higher clock frequencies. Moreover, power consumption is a function of frequency. That is, a faster clock speed results in devices operable with the clock signal to change states more rapidly, consuming increased power as compared to devices operating at lower clock speeds. Accordingly, the higher the clock frequency the more power that is generally consumed.

Some embodiments provide a system clock signal to various components, such as microcontroller 114 and output driver 115. According to the illustrated embodiment, the system clock signal is provided to output driver 115 through microcontroller 114. Accordingly, both microcontroller 114 and output driver 115 are operating synchronously with respect to the same clock signal. Such a configuration is advantageous where synchronization of one or more operations between microcontroller 114 and output driver 115 are desired. However, where a higher clock speed is needed by some components but not by all components, such a configuration can result in unnecessary power consumption.

Accordingly, some embodiments implement a clock configuration in which the clock signal has a frequency less than that of a desired frequency (e.g., ½ a desired frequency) in order to conserve power and/or to provide reliable operation with respect to components requiring lower clock frequencies while providing operation with respect to other components at a desired higher speed. For example, rather than a 100 kilohertz clock desired in the above example for providing control of pulse width to 10 microseconds, an embodiment provides a 50 kilohertz clock to drive circuitry, such as microcontroller 114 at a sufficient speed, thereby conserving power. In order to achieve a desired processing rate, with respect to components for which a higher clock speed is suitable, some embodiments use the rising edge and falling edge of the clock signal to provide a higher clocking rate. Accordingly, in the above example, a 50 kilohertz clock may be relied used to control timing to 10 microseconds. It should be appreciated that the foregoing clocking technique provides a solution which avoids the use of an external high frequency crystal oscillator and clock divider circuitry, thereby facilitating a small system implementation using relatively few components.

Preferred embodiments utilize trim crystal X1 of clock 116 to provide a 50% duty cycle (equal periodicity between high and low portions of the clock signal square wave), such as through proper selection of one or more tuning resistors (e.g., resistors R1 and/or R2), to facilitate use of the rising and falling edges of the clock signal as described above. A resistor selected to provide a 50% duty cycle with respect to clock 16 has current (and thus power) consumption associated with its use. However, it may not be necessary to have a 50% duty cycle provided by the clock signal of clock 116 at all times. For example, although a 50% duty cycle may be desired during delivery of a stimulation pulse by IPG 110, other times of operation with respect to IPG 110 may not substantially benefit from provision of a 50% duty cycle clock signal. However, it may still be desired to have a clock signal during such times, although there may be no requirement that the duty cycle of the clock signal be any particular ratio.

Accordingly, some embodiments include a plurality of tuning resistors, shown as resistors R1 and R2, with respect to crystal X1. Resistor R1 preferably provides a relatively high impedance to minimize current (and thus power) through resistor R1. However, the impedance of resistor R1 is preferably selected to cause oscillation of crystal X1, although perhaps at a duty cycle other than 50%. The impedance of resistor R2 is preferably selected such that, when placed in parallel with resistor R1, crystal X1 oscillates with a 50% duty cycle. Accordingly, a controllable switch (shown here as NMOS FET Q1) is provided with respect to clock 116 to facilitate selection of 50% duty cycle operation when desired. By not selecting 50% duty cycle operation, power consumption associated with clock 116 is decreased. However, when a 50% duty cycle is desired (e.g., when a stimulation pulse is being delivered), clock 116 of the illustrated embodiment is able to provide a clock signal having a 50% duty cycle in response to a control signal.

Voltage Regulator

Directing attention to FIG. 3A, detail with respect to an embodiment of voltage regulator 111 of FIG. 1 is shown. Voltage regulator 111 operates to accept a reference voltage $V_{REF}$, which may be prone to variation in magnitude, and provide an output voltage $V_{OUT}$ having a selected, relatively constant magnitude. For example, $V_{REF}$ may be provided by battery 121 which may have a relatively high voltage when initially charged or put into service and the voltage may sag over the life or charge cycle of the battery. However, circuitry of IPG 110 may malfunction if a voltage applied thereto is not within particular limits, and the high and low voltage extremes associated with battery 121 may be outside of these limits. Accordingly, voltage regulator 111 may operate to regulate $V_{REF}$ as provided by battery 121 to provide $V_{OUT}$ within a range acceptable to circuitry of IPG 110.

In operation, a typical voltage regulator is capable of maintaining an output voltage only when the reference voltage provided thereto is at least slightly higher than the output voltage. However, over the course of a battery's life or charge cycle, the voltage provided thereby may sag to a point too near or below the $V_{OUT}$, causing the voltage regulator output voltage to also sag, and thus the regulator can no longer provide the desired regulated output voltage. However, voltage regulator 111 of the illustrated embodiment is adapted to provide a desired output voltage level even when a reference voltage provided by battery 121 drops below the desired output voltage.

The embodiment of voltage regulator 111 illustrated in FIG. 3A includes multiplexer 310 having $V_B$ (battery voltage) and $2V_B$ (twice the battery voltage) as inputs. For example, $V_B$ may be provided directly by battery 121 and $2V_B$ may be provided by a voltage doubling output of voltage multiplier 151. The Select 1 input to multiplexer 310 selects between $V_B$ and $2V_B$ for output as $V_{REF}$ to regulator 320. Accordingly, if the voltage of battery 121 drops too near or below a level suitable for regulator 320 to reliably provide a desired level $V_{OUT}$, an appropriate signal may be provided at Select 1, such as under control of microcontroller 114, to select $2V_B$, and thus extend the operation of IPG 110 using battery 111.

Some embodiments implement a closed loop control system with respect to voltage regulator 111 in order to provide voltage selection control as described above. For example, sensing circuitry, such as may utilize ADC 620 in making voltage measurements as described below, is utilized according to a preferred embodiment to provide information with respect to the battery voltage $V_B$ (e.g., measuring a present battery voltage). This battery voltage information is preferably provided to a control system, such as may be provided using microcontroller 114, in order to provide appropriate control signals for controlling the output voltage of voltage regulator 111, such as by providing an appropriate "select" signal to multiplexer 310.

It should be appreciated that embodiments may utilize voltages and/or sources other than those described with respect to the illustrated embodiment. For example, where voltage multiplier 15L comprises a fractional voltage multiplier, multiplexer 310 may operate to select a multiple of $V_B$ (e.g., 1¼$V_B$, 1½$V_B$, 1¾$V_B$, 2¼$V_B$, etcetera) most near a desired output voltage which is suitable for use by regulator 320 in providing the desired output voltage. Accordingly, multiplexer 310 of embodiments may utilize a number of inputs different than shown in the illustrated embodiment.

Voltage regulator 111 is adapted to provide dynamic voltage adjustment. Such dynamic voltage adjustment may be useful in providing reduced power consumption while continuing to facilitate features and functions requiring voltage levels which are not conducive to power efficient operation.

For example, microcontroller 114 may include memory registers for storing program or control information which may be changed by "flashing" the memory registers with new values. Such memory flashing may require a higher voltage level, such as 2.7 volts, whereas reliable operation of microcontroller 114 (and/or other components of IPG 110) may be achieved using a lower voltage level, such as 2.2 volts. The components of IPG 110 may be continuously operated at the higher voltage (2.7 volts in the foregoing example), and thus voltage regulator 111 configured to provide $V_{OUT}$ continuously at this level, in order to allow memory flashing when desired. However, the use of this unnecessarily high voltage level during normal operation of IPG 110 results in higher power consumption during such normal operation. If voltage regulator 111 were configured to provide $V_{OUT}$ at the more economical lower level, more efficient operation of IPG 110 would be had, however explanting of IPG 110 may be required to alter the programming thereof. Accordingly, regulator 320 of the illustrated embodiment includes resistor network 321 useful in changing the magnitude of $V_{OUT}$ dynamically under control of a control signal provided at Select 2. Using resistor network 321, some embodiments may provide normal operation of IPG 110 using a lower voltage $V_{OUT}$ for more efficient power consumption, and provide a higher voltage $V_{OUT}$ when needed, such as during memory flashing operations, to provide increased power to a transmit coil when an external programmer is disposed farther away from IPG 110, etcetera.

Directing attention to FIG. 3B, a conceptual diagram showing a configuration of regulator 320 implementing resistor network 321 to provide dynamic adjustment of $V_{OUT}$ according to one embodiment is shown. As shown in FIG. 3B, regulator 320 may be conceptually thought of as an amplifier (shown here as operational amplifier 330) accepting the voltage $V_{REF}$ as an input and providing the voltage $V_{OUT}$ as an output. Feedback resistor 322 and shunt resistor 323 are provided with respect to operational amplifier 330 to control the gain provided thereby. Resistors 322 and 323 of the illustrated embodiment are variable resistors, operable under control of a signal provided to Select 2, to facilitate dynamic selection of $V_{OUT}$ through proper adjustment of resistors 322 and 323.

Although resistors 322 and 323 are shown in the illustrated embodiment as variable resistors disposed in a feedback and shunt configuration, it should be appreciated that resistor network 321 may be implemented in a number of configurations. For example, resistors 322 and/or 323 may comprise a plurality of discrete resistors (e.g., each comprising a resistor associated with a first value of $V_{OUT}$ and another resistor associated with a second value of $V_{OUT}$) selectable under control of Select 2. Moreover, dynamic adjustment of $V_{OUT}$ according to some embodiments may be provided by circuitry in addition to or in the alternative to the illustrated resistor divider network. For example, a resistor capacitor network, and active divider network, etcetera may be utilized according to some embodiments.

Battery Charge Control

Directing attention to FIG. 4A, detail is shown with respect to an embodiment of charge control 122 of power supply 112 shown in FIG. 1. In operation according to some embodiments, battery 121 is recharged by application of a signal to receiver 113. RF signals applied to receiver 113 may comprise data communications, and thus be provided to microcontroller 114, or other components of IPG 110, by near field communication module 431 of receiver 113, or may comprise charging signals, and thus be provided to charge control 122 by RF converter 432. RF energy of a charging signal coming into RF converter 432 is rectified and provided to charge control 122 as a DC signal for charging battery 121. Recharging of battery 121 according to some embodiments is accomplished while IPG 110 remains operational. That is, battery 121 continues to provide power for generation and delivery of stimulation pulses during a charging cycle.

Charge control 122 of the illustrated embodiment includes chopping regulator 421, monitor 422, and current source 423 used in charging battery 121. Chopping regulator 421 of embodiments controls the voltage into the constant current battery charging circuitry ($V_{CHRG}$). Monitor 422 provides monitoring with respect to charging voltage ($V_{CHRG}$) and/or current ($I_1$, $I_2$, and $I_3$) and control of chopping regulator 421, current source 423, and/or an external charger (not shown).

Excessive voltage drops across elements of the charging circuit (e.g., circuitry controlling the charging current, such as a FET) can generate heat which would need to be dissipated into the body where IPG 110 is implanted. Accordingly, chopping regulator 421 of preferred embodiments controls the voltage ($V_{CHRG}$) into the constant current battery charging circuitry (shown here as current source 423) to be close to the present voltage of battery 121 ($V_{PRES}$) while providing a sufficient voltage to charge battery 121. That is, the voltage of chopping regulator 421 of preferred embodiments is controlled to be higher than the present battery voltage $V_{PRES}$, when the battery is to be recharged, in order to establish a charging current with respect to the battery. According to embodiments, this charging voltage $V_{CHRG}$ may be set at or slightly above the battery voltage $V_{BATT}$ to which the battery is to be charged. Alternative embodiments may set the charging voltage $V_{CHRG}$ at a level above the present battery voltage $V_{PRES}$ sufficient to establish a charging current, and continually or periodically increase the charging voltage $V_{CHRG}$ as the present battery voltage $V_{PRES}$ rises due to the battery accepting the charge (e.g., $V_{CHRG}$ may be maintained at $V_{PRES}$+500 mV). The foregoing charging voltages provide a sufficiently low difference between the present battery voltage $V_{PRES}$ and the charging voltage $V_{CHRG}$ during normal battery charging operations to minimize heat generated by charging circuit elements and/or to avoid other undesired effects.

By using a higher charging current, the time required for recharging battery 121 is minimized but results in undercharging due to battery impedance. Accordingly, some embodiments implement a multi-current charging technique, wherein the charging current is reduced each time the battery voltage $V_{PRES}$ reaches a target threshold voltage. Stages of the aforementioned multi-current charging technique may implement the same or different target threshold voltages (e.g., $V_{MAX}$, $V_{BATT}$, etcetera), as desired.

Figure 4B:
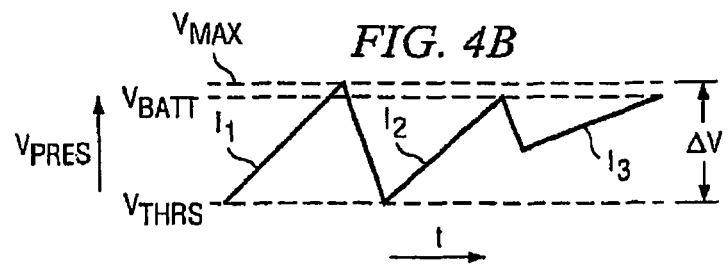
FIG. 4B shows a diagram of voltage verses time for a multi-stage recharge technique of some embodiments.

Directing attention to FIG. 4B, a graph of voltage verses current using a multi-current technique of one embodiment is shown. The embodiment of FIG. 4B utilizes 3 different charging current levels (shown here as $I_1$, $I_2$, and $I_3$), as may be selected at current source 423 under control of monitor 422. According to a preferred embodiment $I_1$ is a 100% charge current (e.g., a maximum charge current as provided by recharging circuitry of stimulation system 100), $I_2$ is a 50% charge current (e.g., one-half the maximum charge current as provided by recharging circuitry of stimulation system 100), and $I_3$ is a 20% charge current (e.g., one-fifth the maximum charge current as provided by recharging circuitry of stimulation system 100).

In the embodiment of FIG. 4B, 100% charge current $I_1$ is initially applied to battery 121 for rapid charging until the present voltage of battery 121 ($V_{PRES}$) reaches a first predetermined target threshold voltage, e.g., maximum battery voltage during charging $V_{MAX}$, as may be determined by monitor 422. Monitor 422 of embodiments may comprise a comparator circuit for comparing a measured voltage against one or more threshold voltages, comparing two or more measured voltages, etcetera. As discussed below; $V_{MAX}$ may be adjustable, such as at various times in the life of battery 121. This maximum voltage is preferably selected to provide charging of battery 121 to a desired battery voltage level (e.g., $V_{BATT}$) within an acceptable amount of time. For example, $V_{MAX}$ of some embodiments is selected to be in the range of 4.05-4.122 volts where a battery voltage $V_{BATT}$ of 4.05 volts is implemented. According to a preferred embodiment, $V_{MAX}$ is selected to be the battery voltage $V_{BATT}$ in the early life of the battery and is increased periodically as the battery ages, reaching a maximum value at the battery end-of-life. Such an embodiment may be utilized to provide substantially constant recharging times throughout the life of the battery, as will be better appreciated from the discussion below.

It should be appreciated that the aforementioned charging voltage $V_{CHRG}$ provided by chopping regulator 421 of preferred embodiments may be different than the predetermined maximum battery voltage $V_{MAX}$. For example, the charging voltage $V_{CHRG}$ may be selected to be slightly larger than the predetermined maximum battery voltage $V_{MAX}$ in order to facilitate a charging current with respect to battery 121 throughout the present battery voltage $V_{PRES}$ rising to the predetermined maximum battery voltage $V_{MAX}$. As discussed above, the charging voltage $V_{CHRG}$ may be varied during charging, and thus may be lower than the predetermined maximum battery voltage $V_{MAX}$ at times in the charge cycle, although providing a voltage difference with respect to the present battery voltage $V_{PRES}$ sufficient to facilitate a charging current.

When the present battery voltage $V_{PRES}$ reaches the predetermined maximum voltage $V_{MAX}$, monitor 422 of a preferred embodiment controls current source 423 to step down to 50% charge current $I_2$ for slower, more complete charging. Current $I_2$ is preferably applied until another predetermined target threshold voltage, e.g., battery voltage $V_{BATT}$, is reached, as may be determined by monitor 422. When the battery voltage $V_{BATT}$ is reached in the illustrated embodiment, monitor 422 of a preferred embodiment controls current source 423 to step down to 20% charge current $I_3$, for still slower, more complete charging. Current $I_3$ is preferably applied until another predetermined target threshold voltage, e.g., battery voltage $V_{BATT}$, is reached. Once the battery voltage $V_{BATT}$ is again reached in the illustrated embodiment, charging according to the illustrated embodiment is complete.

It should be appreciated that the multi-current charging technique described above provides substantially complete recharging of battery 121 in a minimal amount of time without introducing excessively high voltages. Specifically, the initial charging current is a relatively high current to provide rapid charging of battery 121. However, in order to provide for complete charging of battery 121, without use of a high charging voltage $V_{CHRG}$ (such as may result in heating of charging circuit components), a lower current is subsequently used in charging battery 121 when a predetermined target threshold voltage is reached. The use of an intermediate current in the second charging phase facilitates relatively rapid continued charging of battery 121, again without use of a high charging voltage $V_{CHRG}$. The use of a relatively low current in the final charging phase facilitates substantially complete charging of battery 121 without requiring an unacceptably long charge time, since the previously applied higher charging currents have substantially replenished battery 121.

Some embodiments employ lithium-ion chemistry, or similar battery technology, with respect to battery 121. Experimentation has revealed that the impedance of a lithium-ion battery is related to the capacity of the battery and the age related degradation of the battery. Other battery chemistries provide similar relationships between impedance, charge rate, etcetera and the capacity of the battery and the age related degradation of the battery. Some embodiments utilize the foregoing information in recharging the battery, such as to improve efficiency. For example, some embodiments may utilize information correlating battery impedance, battery capacity, and/or age related degradation, as may be stored in a table of battery characteristics, to provide a substantially constant recharging time, substantially constant battery capacity, etcetera throughout the service life of the battery.

According to some embodiments, a predetermined target threshold voltage, e.g., $V_{MAX}$ in the above example, used in determining the end of one or more charge current stages (e.g., when to transition from charge current $I_1$ to $I_2$ in the example above) is programmable. For example, where a 4.05 volt battery voltage $V_{BATT}$ is being used, $V_{MAX}$ may be programmable between 4.05 and 4.122 volts. The use of a lower voltage $V_{MAX}$ at times early in a battery's life according to some embodiments provides acceptable recharge times while minimizing the charging voltage (and thus undesirable effects such as excessive heat generation), whereas a higher voltage $V_{MAX}$ at times later in a battery's life can be selected to provide a balance between recharge times and the charging voltage (and thus provide reasonable charging times without unacceptable effects).

In explaining the foregoing, attention is directed again to FIG. 4B. It can be seen in FIG. 4B that when the charging current is changed, such as from $I_1$ to $I_2$, the present battery voltage $V_{PRES}$ drops. This difference in voltage or $\Delta V$ is a function of the charge impedance of the battery, and thus is related to the age and capacity of the battery. It should be appreciated that, the larger the $\Delta V$, the longer it will take a subsequent charging current, e.g., $I_2$, to reach a target threshold voltage, such as the desired battery voltage $V_{BATT}$. Accordingly, some embodiments may operate to measure $\Delta V$, such as by operation of monitor 422, and to adjust the predetermined maximum voltage $V_{MAX}$ when $\Delta V$ is determined to be sufficiently large to require an unacceptable period for a subsequent charge current to cause the present battery voltage $V_{PRES}$ to reach the desired battery voltage $V_{BATT}$. Some embodiments implement the predetermined maximum voltage $V_{MAX}$ with respect to a first charging stage, or one or more early charging stages, because the $\Delta V$ of such an initial stage or earlier stages will be greater due to the battery impedance and the use of a higher charging current. Later charging stages are less likely to be substantially impacted by a slight increase in the target threshold voltage due to their use of appreciably lower charging currents. However, alternative embodiments may implement programmable target threshold voltages and/or different target threshold voltages with respect to one or more charging states. For example, target threshold voltages used for each stage of a multi-current charging technique implemented according to one embodiment may decrease target threshold voltages of subsequent charging stages by an amount corresponding to a reduction in the charging current between charging stages.

Some embodiments operate to measure one or more threshold voltages $V_{THRS}$ in determining when to adjust a target threshold voltage such as $V_{MAX}$, rather than directly measuring $\Delta V$. In operation according to such embodiments, the target threshold voltage is known. Accordingly, a threshold voltage $V_{THRS}$ may be selected, and measured by monitor 422, such that when the present battery voltage $V_{PRES}$ drops below this threshold level during charging one or more target threshold voltage, e.g., $V_{MAX}$, is adjusted upward for subsequent charge cycles.

The foregoing $\Delta V$ and $V_{THRS}$ values have application in addition to selection of a new target threshold voltage according to some embodiments. Because $\Delta V$, and thus the present battery voltage $V_{PRES}$ dropping below $V_{THRS}$, are a function of the charge impedance of the battery, they are an indication of the capacity and/or age of the battery. Accordingly, a $\Delta V$ or threshold voltage $V_{THRS}$ may be selected according to some embodiments to indicate a near end-of-life of battery 121, such as to trigger an alarm to indicate an impending need to replace the battery, to alter operation of IPG 110, etcetera.

It should be appreciated that, although the illustrated embodiment is shown to utilize three charging currents providing 100%, 50%, and 20% charging current, some embodiments may implement any number of charging currents in any magnitudes determined desirable for a particular application. Likewise, some embodiments are not limited to the particular number of target threshold voltages, voltage differences, threshold voltages, and voltage magnitudes described with respect to the exemplary embodiment. For example, some embodiments may implement a series of target threshold voltages, such as for use at beginning-of-life, middle-of-life, and end-of-life. According to some embodiments, a target threshold voltage such as $V_{MAX}$ is incremented in predetermined steps (e.g., 20 millivolt steps, 48 millivolt steps, etcetera) when a $\Delta V$ greater than a particular magnitude is encountered between charge stages or when $V_{THRS}$ is crossed between charge states. Similarly, a plurality of $\Delta V$ or threshold voltages $V_{THRS}$ may be implemented, if desired.

It should be appreciated that, although current source 423 of the illustrated embodiment preferably provides a constant current to battery 121 for charging, current source 423 of a preferred embodiment comprises a variable current source. That is, current source 423 of a preferred embodiment is controllable to provide a selected current (e.g., including $I_1$, $I_2$, and $I_3$) which, once selected, is provided as a constant current.

The duty cycle of chopping regulator 421 required to reduce the input voltage level to a desired voltage level (e.g., $V_{BATT}$+(0.1-0.5 volts)) is directly related to the amount of RF energy coming in from RE converter 432. Accordingly, monitor 422 of embodiments may analyze the duty cycle of chopping regulator 421 to determine the strength of the RF charging signal. Monitor 422 may provide a control signal to the external charger providing the RE charging signal (e.g., through microcontroller 114 and near field communication 431) to cause the external charger to reduce its power output. Such a configuration allows the external charger to conserve energy, which may be particularly beneficial where the external charger is itself battery powered.

Monitor 422 of some embodiments provides monitoring with respect to operation of IPG 110 in addition to or in the alternative to charging operations. For example, monitor 422 may monitor a level of battery 121 during normal operations and detect when the battery should be recharged, when the battery level is such that pulse generation should be suspended, etcetera. Monitor 422 may, for example, provide a control signal to microcontroller 114 when battery 121 drops below a level of a recharge threshold. Microcontroller 114 may then provide an alarm or other indication to a user to notify the user that battery 121 should be recharged. Monitor 422 may continue to monitor battery 121 which, if recharging is not provided, may drop below a second threshold. A control signal may be provided to microcontroller 114 by monitor 422 to indicate that this second threshold has been passed and, in response, microcontroller 114 may suspend certain operations in order to conserve sufficient battery capacity to maintain critical functions, such as retaining an operating program of IPG 110. The foregoing thresholds monitored by monitor 422 may be adjusted depending upon the age and/or capacity of battery 121, as may be determined using $\Delta V$ and/or $V_{THRS}$ as described above.

Voltage Multiplier Output Voltage

Figure 5:
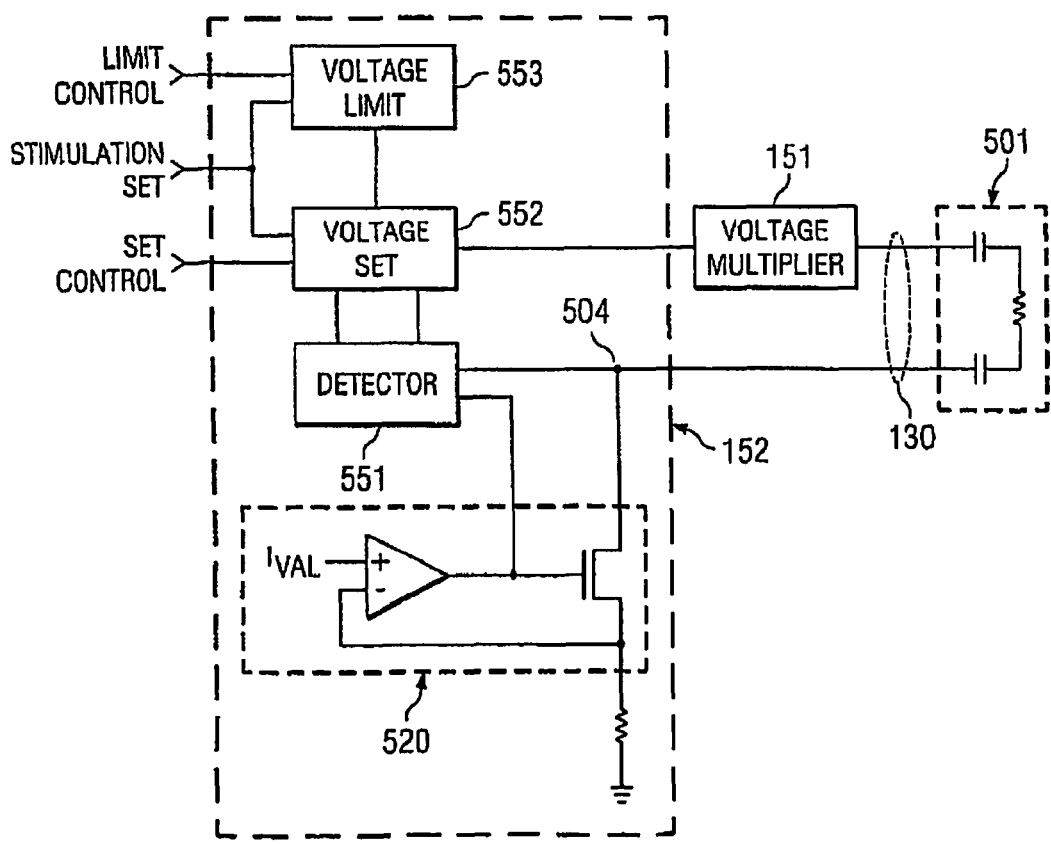
FIG. 5 shows additional detail with respect to a voltage/current control circuit of the system of FIG. 1 according to some embodiments.

Directing attention to FIG. 5, detail with respect to an embodiment of voltage/current control 152 of FIG. 1 for providing voltage multiplier voltage control is shown. Voltage/current control 152 of the illustrated embodiment provides automatic and manual voltage control, allowing incrementing and decrementing of the output voltage, with respect to voltage multiplier 151. In a manual mode of one embodiment, the output voltage setting is controlled by microcontroller 114 providing a set control signal to voltage/current control 152. Accordingly, in this manual mode, microcontroller 114 is involved in the changes to the output voltage of voltage multiplier 151 in terms of incrementing or decrementing the values. However, in an automatic mode of one embodiment, voltage/current control 152 controls the changes to the output voltage of voltage multiplier 151, and thus there need not be any processing overhead on the part of microcontroller 114 to determine the optimal value for the output voltage of voltage multiplier 151.

Voltage multiplier 151 utilized according to some embodiments preferably comprises a fractional voltage multiplier, such as may provide output voltages in fractional multiples of a supply voltage (e.g., $\frac{1}{4}V_{BATT}$, $\frac{1}{2}V_{BATT}$, $\frac{3}{4}V_{BATT}$, $V_{BATT}$, $1\frac{1}{4}V_{BATT}$, $1\frac{1}{2}V_{BATT}$, $1\frac{3}{4}V_{BATT}$, $2V_{BATT}$, $2\frac{1}{4}V_{BATT}$, $2\frac{1}{2}V_{BATT}$, $2\frac{3}{4}V_{BATT}$, $3V_{BATT}$, $3\frac{1}{4}V_{BATT}$, $3\frac{1}{2}V_{BATT}$, $3\frac{3}{4}V_{BATT}$, etcetera). Additional detail with respect to fractional voltage multipliers as may be utilized according to some embodiments is provided in the above referenced patent applications entitled "EFFICIENT FRACTIONAL VOLTAGE CONVERTER" and "FRACTIONAL VOLTAGE CONVERTER." In particular, the foregoing application entitled "EFFICIENT FRACTIONAL VOLTAGE CONVERTER" discloses a voltage source provided as a stacked voltage multiplier which stacks voltages to create a desired voltage upon demand and, immediately after providing a voltage pulse, is unstacked back to its primary voltage components.

In operation of IPG 110 according to some embodiments, a goal is to provide a power source to deliver a particular amount of current to load 501 (such as may comprise a portion of a human body into which lead 130 is implanted) via selected ones of electrodes 132-135. It should be appreciated that, as set forth in Ohm's law, a particular amount of voltage provided by voltage multiplier 151 will be needed to deliver a desired level of current through load 501. However, providing a voltage level substantially in excess of the voltage needed to deliver the desired current may be undesirable. For example, voltage in excess to that needed for delivery of the desired current may be dissipated as heat or otherwise sunk, thereby resulting in inefficient use of energy from battery 121. Moreover, if the output voltage provided by voltage multiplier 151 were not set to a limit somewhat near that needed to deliver the desired current, a change in load 501 (such as by movement of lead 130 within the patient) could result in over stimulation or other undesired results.

Accordingly, voltage multiplier 151 and voltage/current control 152 of some embodiments cooperate to provide a voltage limited, constant current source. In providing the foregoing, voltage/current control 152 of the illustrated embodiment comprises detector 551 that monitors voltages as provided by voltage multiplier 151. When it is determined that the output voltage of voltage multiplier 151 is in excess (perhaps by a predetermined amount, such as a fractional voltage step amount) of what is needed to provide a desired current, detector 551 can provide a control signal to voltage set 552 to decrement the voltage. Voltage set 552 may, in turn, provide a control signal to voltage multiplier 151 to select an appropriate, lower, voltage (perhaps in one or more decremental steps). Similarly, when it is determined that the output voltage of voltage multiplier 151 is below what is needed to provide a desired current, detector 551 can provide a control signal to voltage set 552 to increment the voltage. Voltage set 552 may, in turn, provide a control signal to voltage multiplier 151 to select an appropriate, higher, voltage (perhaps in one or more incremental steps).

Feed back circuit 520 provides detail with respect to providing information to detector 551 useful in making voltage increment/decrement determinations. The control loop of feedback circuit 520 is trying to sink the desired current $I_{VAL}$. However, where the output voltage of voltage multiplier 151 is too low to achieve delivery of the desired current to load 501, feedback circuit 520 is unable to sink $I_{VAL}$ (it is limited by the voltage of voltage multiplier 151).

Accordingly, a current error is generated and provided to detector 551. Conversely, where the output voltage of voltage multiplier 151 is higher than needed to achieve delivery of the desired current to load 501, feedback circuit 520 will be able to sink $I_{VAL}$, but excess voltage will be present at node 504. Accordingly, detector 551 may use current error and voltage information in determining when to increment or decrement an output voltage of voltage multiplier 151.

The foregoing voltage incrementing could result in a voltage output provided by voltage multiplier 151 being undesirably high. For example, lead 130 may move or shift within the body in which it is implanted, thus appreciably changing the impedance of load 501. Detector 551 may detect that the desired current has not been delivered, without determining that the impedance of load 501 has changed, and thus may control voltage multiplier 151 to output a voltage higher than that desired to be delivered to the load. Accordingly, a voltage limit may be set by voltage limit 553, such as may be provided by a control signal applied thereto.

In operation according to a preferred embodiment, voltage limit 553 sets a limit beyond which voltage/current control 152 cannot, by itself increment the output voltage. Accordingly, when a voltage limit set by voltage limit 553 is reached, voltage/current control 152 may provide a control signal to microcontroller 114, such as to notify an operator of the limit being reached, for a determination with respect to whether the limit should be adjusted, etcetera.

The foregoing voltage limits are preferably set with respect to each stimulation set implemented by IPG 110. For example, a clinician may establish a voltage limit, such as some percentage of or slightly higher than a stimulation voltage, for each stimulation set employed. These voltage limits may be provided to voltage limit 553 by microcontroller 114.

Additionally, microcontroller 114, a clinician, or other user may manually provide voltage selection with respect to voltage multiplier 151, such as during trial stimulation, etcetera. Accordingly, a voltage set control signal may be provided to voltage set 552, such as by microcontroller 114, to override voltage selection as provided by detector 551, if desired.

It should be appreciated that setting the output voltage of voltage multiplier 151 near that needed to deliver a desired current to load 501 has advantages in addition to safety/comfort. For example, by setting the output voltage near that needed to deliver a desired current can result in significant energy savings, which may be very important where IPG 110 is powered by a battery. The use of a fractional multiplier according to some embodiments facilitates the foregoing energy savings because, unlike typical voltage multipliers, voltage step sizes in fractions of a supply voltage are possible, and thus selection of an output voltage very near that needed to deliver a desired current is possible.

The foregoing circuitry may be utilized in providing functionality in addition to or in the alternative to voltage multiplier voltage control. For example, measurement of a voltage at node 502 prior to reversing the connection of load 501 for active discharge and after reversing the connection of load 501 for active discharge may be used to provide an inverted electrode check. Specifically, the voltage at node 502 should change when the anode and cathode connections of load 501 are reversed. Accordingly, providing the above mentioned check of the voltage at node 502 may be used to verify that the reversed connection has properly taken place, such as to avoid delivering two stimulation pulses rather than a stimulation pulse and an active discharge pulse.

Another technique for providing an inverted electrode check according to some embodiments comprises using a sampling capacitor sampling the electrode voltage by being coupled across the anode and cathode connections to load 501. The voltage stored upon the sampling capacitor will have a polarity consistent with the anode/cathode orientation of the electrodes of load 501. The sampling capacitor may be coupled to a comparator, such as that of feed back circuit 520, to provide information with respect to the electrode configuration. For example, the capacitor lead expected to have a positive charge if the electrodes of load 501 were switched in the proper orientation may be coupled to the positive (+) input of the comparator and the lead expected to have a negative charge if the electrodes of load 501 were switched in the proper orientation may be coupled to the negative (−) input of the comparator. According to embodiments, if the polarity of the electrodes of load 501 were configured as expected when sampled, the result of the comparison should be positive. However, if the polarity of the electrodes of load 501 were not configured as expected (i.e., reverse polarity voltage is sampled), the result of the comparison should be negative. Accordingly, a determination with respect to there being an inverted electrode may be made from the output of the aforementioned comparator.

Housing Electrode

Embodiments of IPG 110 are housed within a hermetically sealed container having at least a portion of which is electrically conductive. Referring again to FIG. 1, housing 117 of the illustrated embodiment comprises a metal "can" surrounding components of IPG 117. Housing 117 of the illustrated embodiment is electrically coupled to output driver 115 so as to allow the use of housing 117 as an electrode during delivery of pulses. The use of housing 117 as an electrode, particularly as an anode, facilitates the use of a monopole electrode configuration with respect to lead 130, as may be useful in deep brain stimulation or other desirable tissue stimulation situations.

According to one embodiment, housing 117 is selectable as an anode, a cathode, or disconnected from the delivery of a pulse. Housing 117 may therefore be utilized in an active discharge pulse delivery scheme. For example, housing 117 may be configured as an anode during a stimulation pulse and then reconfigured as a cathode during a corresponding active discharge pulse. Such a configuration facilitates increased frequency and/or amplitude monopole stimulation.

Some embodiments provide programming to restrict configuring housing 117 as a cathode to particular pulses, such as the aforementioned active discharge pulse. For example, it may be desired to prevent configuration of housing 117 as a cathode during a stimulation pulse, such as to prevent stimulation of tissue surrounding housing 117. Accordingly, some embodiments operate to prevent patent or physician selection of housing 117 as a cathode. Control systems, such as microcontroller 114, of embodiments operate to automatically configure housing 117 as a cathode at an appropriate time, such as to provide active discharge for monopole stimulation where, due to stimulation frequency and/or stimulation amplitude, charge is accumulating. Accordingly, configuration of housing 17 as a cathode according to some embodiments is circuit determinable.

Stored Energy Discharge

Figure 6A:
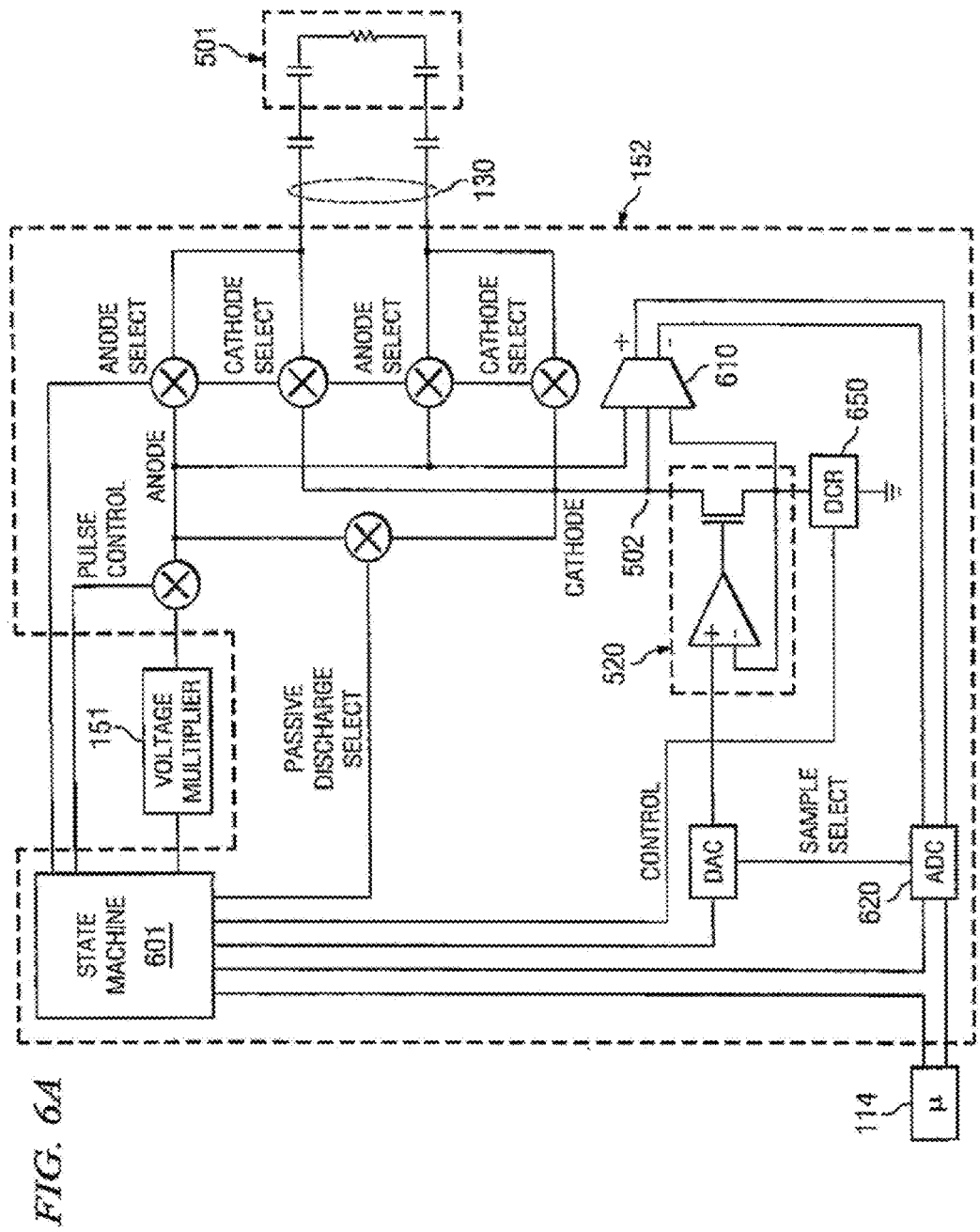
Figure 7A:
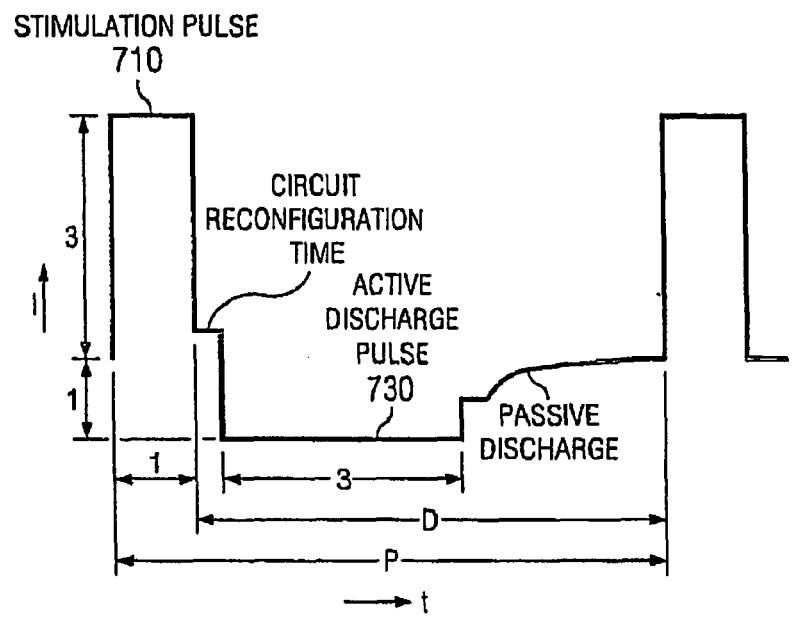
Figure 7B:
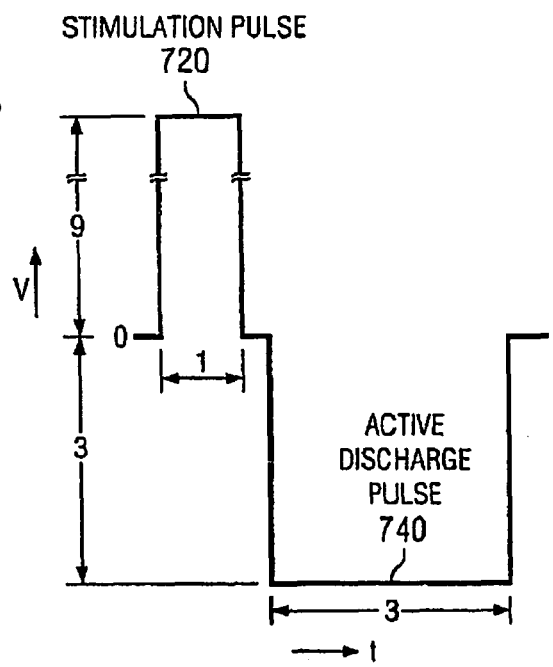

Directing attention to FIG. 6A, detail with respect to an embodiment of voltage/current control 152 of FIG. 1 for providing discharge of energy stored within a capacitance of the load and IPG circuitry is shown. Voltage/current control 152 of the illustrated embodiment provides selection between, and control of, passive discharge (i.e., the connecting the anode and cathodes together) and active discharge (i.e., the reversing of current and voltage to actively remove the charge stored in the capacitance) modes, pulse control with respect to stimulation pulses and discharge pulses, and pulse shaping with respect to stimulation pulses and discharge pulses to provide efficient operation of IPG 110. FIGS. 7A-7C show timing diagrams with respect to pulse (both stimulation and active discharge pulses) current (FIG. 7A) and voltage FIGS. 7B and 7C), as provided to the patient load, by operation of voltage/current control 152 of FIG. 6A according to some embodiments.

Figure 9:
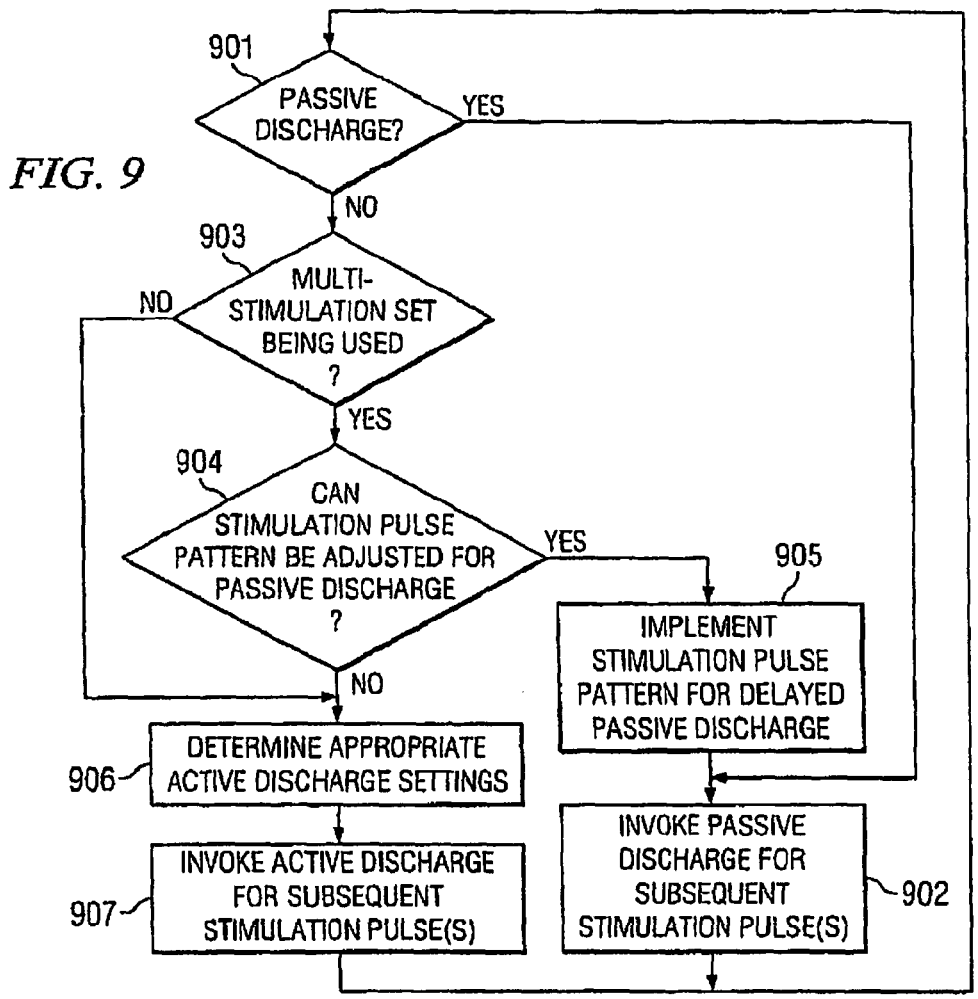
FIG. 9 shows a high level flow diagram of operation of one embodiment in determining when to invoke passive and active discharging techniques.

As stimulation pulses having a current and voltage magnitude (e.g., 3 milliamps stimulation pulse current magnitude 710 of FIG. 7A and 9 volts stimulation pulse voltage magnitude 720 of FIGS. 7B and 7C) and duration (e.g., 1 millisecond in FIGS. 7A-7C) associated therewith are delivered to load 501 at a selected frequency (period P of FIG. 7A), charge may accumulate within the capacitance of the load and other circuitry. Although this charge will dissipate with time, there may be insufficient time (D of FIG. 7A) between stimulation pulses to allow sufficient discharging for a subsequent stimulation pulse to deliver a desired amount of current. Accordingly, active discharging may be needed to effectively provide high frequency stimulation pulses. However, active discharging involves the use of energy not directly used in delivering therapy to the patient and, therefore, is a less energy efficient mode of operation than is passive discharge. For example, a typical active discharge pulse will be provided in a 1:1 relationship to a stimulation pulse (i.e., at a same current level for a same duration of time, although in a reverse polarity, e.g., 3 milliamps and 9 volts for a duration of 1 millisecond, but having opposite polarity to the stimulation pulse, for the example stimulation pulse in FIGS. 7A-7C) to provide complete discharge of energy stored during the stimulation pulse (i.e., provides full charge balance). Such active discharge results in use of 200% of the energy required for the desired stimulation therapy (100% for the stimulation therapy and 100% for the active discharge).

In order to conserve energy, a typical active discharge scheme may not implement active discharging at all times, but rather implement active discharging when the stimulation frequency exceeds some predetermined threshold. Although such a configuration provides some energy savings, use of a stimulation pulse frequency threshold may result in implementing active discharging when active discharge is not required. For example, the stimulation frequency alone does not take into account the stimulation voltage, the stimulation pulse width, the capacitance associated with the load, the impedance of the load, and other variables affecting the time constant of passive discharge. Accordingly, energy may be used in providing active discharging when active discharge is unnecessary.

Some embodiments implement circuitry within voltage/current control 152 which, under control of state machine 601, operates to select between passive and active discharge modes for more efficient operation of IPG 110. For example, multiplexer 610 may be controlled to couple the anode and cathode to analog-to-digital converter (ADC) 620 at a point just before a stimulation pulse is provided and after the anode and cathode are decoupled from a passive discharge state. Accordingly, ADC 620 may output an indication of the charge remaining on the capacitance to state machine 601 (e.g., ADC 620 may be programmed to operate as a 1 bit comparator, comparing the voltage of the charge remaining to one or more predetermined values determined to allow delivery of a desired current, or to a maximum charge imbalance limit). If the charge remaining is greater than a value determined to allow delivery of a desired current, state machine 601 may operate to implement active discharge with respect to one or more subsequent stimulation pulses. Additionally or alternatively, if the charge remaining is determined to be increasing from pulse to pulse at or greater than a particular rate, state machine 601 may operate to implement active discharge with respect to one or more subsequent stimulation pulses.

Some embodiments continue to implement passive discharge techniques even when active discharging has been implemented. For example, during time remaining after an active discharge pulse has been delivered, but before a subsequent stimulation pulse is delivered, some embodiments may couple the anode and cathode to provide passive discharging with respect to an amount of remaining charge. However, some embodiments may not implement passive discharge, such as where active discharge provides full charge balance.

Determination of the charge remaining on the capacitance may be made after each stimulation pulse or after select stimulation pulses. For example, some embodiments may operate to implement determination of the charge remaining on the capacitance after a stimulation frequency is greater than a predetermined threshold (i.e., period P of FIG. 7A is less than a predetermined threshold), or the time between subsequent stimulation pulses (i.e., D of FIG. 7A) is less than a predetermined duration, determined to be indicative of a situation in which passive discharge may be insufficient to provide adequate discharging of the capacitance. Additionally or alternatively, embodiments may operate to implement determination of the charge remaining on the capacitance after a stimulation current and/or voltage is greater than a predetermined threshold determined to be indicative of a situation in which passive discharge may be insufficient to provide adequate discharging of the capacitance.

From the above, it should be appreciated that some embodiments may operate to provide a plurality of passive/active discharge determinations. For example, certain combinations of stimulation frequency and/or magnitude (e.g., stimulation pulse current amplitude<0.8 milliamps and stimulation pulse frequency<250 Hz) may be used in a passive/active discharge determination to invoke only passive discharge based upon the stimulation frequency and/or magnitude settings. Similarly, certain combinations of stimulation frequency and/or magnitude (e.g., stimulation pulse current amplitude>16 milliamps and stimulation pulse frequency>600 Hz) may be used in a passive/active discharge determination to implement active discharge based upon the stimulation frequency and/or magnitude settings. However, combinations of stimulation frequency and/or magnitude falling between the foregoing may result in measurement of voltage remaining on the capacitance (e.g., instantaneous voltage on the capacitance, change in measured voltage on the capacitance over time) or other real-time measurement of actual charge accumulation in order to determine when active discharge should be implemented. Such embodiments provide economic operation of IPG 110 because a determination regarding active discharge utilizing real-time measurements and appreciable processing overhead (e.g., the third active/passive discharge determination case set forth above) may not be made where it is otherwise clear that active discharge should or should not be invoked.

It should be appreciated that in the foregoing example, active discharge may not be implemented even when some charge remains on the capacitance. It has been discovered that some amount of charge may remain on the capacitance without resulting in charge accumulation which prevents delivery of desired currents during stimulation pulses or detrimental charge imbalance between electrodes. Accordingly, state machine 601 of a preferred embodiment does not implement active discharging until a charge remaining on the capacitance just before delivery of a subsequent stimulation pulse is greater than a threshold value.

When active discharging is activated, active discharge pulses utilized according to some embodiments of may be provided in configurations other than the 1:1 correlation to a stimulation pulse described above. For example, some embodiments may implement 1:1, 1:2, 1:3, and 1:4 active discharge configurations (the use of non-one-to-one active discharge pulses is also described in the above referenced patent application entitled "ACTIVE DISCHARGE SYSTEMS AND METHODS"). FIGS. 7A and 7B show an embodiment wherein a 1:3 active discharge configuration is implemented. Specifically, a stimulation pulse having 3 milliamps stimulation pulse current magnitude 710 (FIG. 7A) and 9 volts stimulation pulse voltage magnitude 720 (FIG. 7B) and duration of 1 millisecond (FIGS. 7A and 7B) is provided a corresponding active discharge pulse having 1 milliamp discharge pulse current magnitude 730 (FIG. 7A) and 3 volts discharge pulse voltage magnitude 740 (FIG. 7B) and duration of 3 milliseconds (FIGS. 7A and 7B). It should be appreciated that the foregoing example provides a current which over the time of the discharge pulse is sufficient result in full charge balance (i.e., remove all the charge resulting from the stimulation pulse). However, as discussed above, some amount of charge may remain on the capacitance without affecting the current of a subsequent stimulation pulse. Accordingly, some embodiments may operate to select a discharge pulse voltage magnitude which is less than that needed to deliver a discharge pulse current which, over the time of the discharge pulse, removes all of the charge resulting from the stimulation pulse, but which removes sufficient charge to permit subsequent stimulation pulses to deliver a desired current Utilization of a fractional voltage multiplier, as shown in more detail in the above referenced patent applications entitled "EFFICIENT FRACTIONAL VOLTAGE CONVERTER" and "FRACTIONAL VOLTAGE CONVERTER," as voltage multiplier 151 facilitates energy savings when the foregoing active discharge configurations are implemented by providing selection of output voltage in fractional multiples of a supply voltage. In particular, fractional voltage multipliers as shown in the above referenced patent applications facilitate providing a discharge pulse voltage magnitude very near a minimum voltage determined to that determined to provide desired discharging of the capacitance.

As may be appreciated from the above discussion, in 1:2, 1:3, and 1:4 active discharge configurations of some embodiments, the current utilized in delivering the discharge current is reduced to be 1/X times (where X is 2, 3, or 4, respectively) while the duration of the active discharge pulse is extended to be X times the stimulation pulse duration (where X is again 2, 3, or 4, respectively). Accordingly, a same charge is delivered in the active discharge pulse as was delivered in a stimulation pulse. However, a lower voltage may be utilized in providing the lower current of the active discharge pulse, thereby providing energy savings. By selecting X to provide a pulse duration of sufficient brevity to provide discharge between stimulation pulses, an appreciable amount of power can be conserved by active discharge. For example, assuming the voltage used in providing the active discharge pulse can be controlled to a value sufficient to provide the selected discharge current without providing excess voltage, rather than 200% power associated with 1:1 active discharge, 1:2 provides 150%, 1:3 provides 133%, and 1:4 provides 125%. An optimum active discharge configuration may be automatically selected through the use of adaptive control, lookup tables, etcetera. An approximate optimal value for X may be calculated according to some embodiments according to the formula X=(pulse frequency/pulse width)−1. Additional detail with respect to active discharge systems and methods as may be implemented according to some embodiments is provided in the above referenced patent application entitled "ACTIVE DISCHARGE SYSTEMS AND METHODS."

In many situations, the above mentioned 1:3 active discharge configuration provides optimum efficiency in a large number of situations wherein IPG 110 is expected to be employed. For example, the duration of the active discharge pulse in the 1:4 configuration may be too long for implementation with respect to many stimulation sets. Although effective at providing discharge, the 1:2 configuration often provides a discharge period appreciably less than necessary to provide effective discharge, thus wasting energy due to a higher voltage used in providing the higher current. Accordingly, the 1:3 active discharge configuration may be preferred for use in many situations Some embodiments implement a thermometer code architecture with respect to digitally controlled resistor 650 to facilitate selection between different adaptive discharge configurations, such as the aforementioned 1:1, 1:2, 1:3, and 1:4, on a pulse by pulse or other basis.

Some embodiments implement circuitry within voltage/current control 152, which, under control of state machine 161, operates to select an appropriate active discharge configuration. This minimizes energy consumption while providing sufficient discharge of the capacitance to deliver a desired current in a subsequent stimulation pulse. Accordingly, preferred embodiments not only operate to select an active discharge current ratio with respect to the stimulation pulse (e.g., the aforementioned 1:1, 1:2, 1:3, 1:4, etcetera), but also operate to minimize the voltages used in providing the active discharge current on a pulse by pulse basis or other selectable basis.

Directing attention to FIG. 6B, a simplified functional block diagram, corresponding to the system shown in FIG. 6A, is shown for use in understanding the concepts of adaptive active discharging according to some embodiments. Operation of the system illustrated in FIG. 6B will be described with reference to the exemplary current and voltage timing diagrams of FIGS. 7A and 7C to aid the reader in understanding the concepts of adaptive active discharging as provided according to some embodiments.

In delivering a stimulation pulse, anode select switch 602 and cathode select switch 605 are closed and cathode select switch 603 and anode select switch 604 are open to deliver an anodic stimulation pulse to load 501. Although the use of switches are described with respect to the illustrated embodiment, it should be appreciated that some embodiments may operate without switching circuitry. For example, multiple pulse generators may be utilized within IPG 110, such as to provide a pulse generator for delivering a stimulation pulse and another pulse generator for delivering an active discharge pulse.

The stimulation pulse preferably has a predetermined current, voltage, and duration. For example, in the example illustrated in FIGS. 7A-7B, the stimulation pulse has a current magnitude of 3 milliamps (stimulation pulse current magnitude 710 of FIG. 7A), a voltage magnitude of 9 volts (stimulation pulse voltage magnitude 720 of FIG. 7C), and a duration of 1 (e.g., 1 millisecond as shown in FIGS. 7A and 7C). This stimulation pulse (or other stimulation pulse configurations) may be repeated in period P. In the time between successive stimulation pulses (D), active discharging may be implemented as described above. Accordingly, after delivery of a stimulation pulse, anode select switch 602 and cathode select switch 605 may be opened and cathode select switch 603 and anode select switch 604 may be closed to reverse the polarity and thus deliver a cathodic active discharge pulse to load 501. As previously mentioned, the active discharge pulse preferably provides a same charge (or nearly the same charge) as the corresponding stimulation pulse. Accordingly, the active discharge pulse illustrated in FIG. 7A has a current magnitude 730 of 1 milliamp delivered for a duration of 3 milliseconds, thereby providing a 1:3 active discharge configuration in this example. Because the active discharge current is less, the voltage required to deliver the active discharge current may also be less. Accordingly, an active discharge pulse may comprise a voltage magnitude of 3 volts for the aforementioned duration of 3 milliseconds, as discussed above with respect to FIG. 7B.

Although the foregoing active discharge configuration provides energy savings, assuming that a voltage multiplier or other voltage source, is capable of providing reduced voltage levels as appropriate for an active discharge pulse, further economies may be realized through dynamically adjusting the voltage during an active discharge pulse, thereby providing an adaptive active discharge pulse according to some embodiments. Adaptive active discharge techniques of some embodiments operate to provide a constant discharge pulse current ($I_{DIS}$), and provide a minimum discharge pulse voltage ($V_{DIS}$) to facilitate the desired discharge pulse current (e.g., the magnitude of $I_{DIS}$ selected to provide discharge or charge balance of the capacitance over the duration of the adaptive active discharge pulse). In facilitating the foregoing, it was realized that a voltage is stored on the capacitance to be discharged. When using a constant current to provide active discharge, this voltage depletes linearly. Accordingly, various patterns or phases of active discharge voltage may be implemented to optimize energy usage associated with active discharging.

Directing attention to FIGS. 7C-7F, an exemplary embodiment wherein 3 phases 751, 752, and 753 of active discharge pulse ($V_{DIS}$) 750 are implemented is shown. Specifically, at a first phase of the active discharge pulse (associated with discharge pulse voltage magnitude 751 and portion 703 of $V_{CAP}$ discharge line 702 of FIG. 7D), it was determined that the voltage ($V_{CAP}$) stored on the capacitance to be discharged is itself sufficient to facilitate the active discharge current ($I_{DIS}$). For example, a measurement may be made using multiplexer 610 and ADC 620, as described above, after delivery of the stimulation pulse but prior to implementing the active discharge pulse and a determination made that the magnitude of the capacitance voltage ($V_{CAP}$) is sufficiently greater than a voltage ($V_I$) needed to deliver the constant current active discharge current ($I_{DIS}$) and thus may be initially used to provide the discharge voltage ($V_{DIS}$) without additional voltage being provided by IPG 110.

Anode source 640 (such as may comprise voltage multiplier 151) of a preferred embodiment includes an anode to ground setting (reversing the voltage of the capacitance as seen by circuitry of IPG 110) to facilitate use of the stored voltage with the active discharge current provided by current source 630 to provide active discharging of the capacitance during the first phase of the adaptive active discharge pulse. As the stored voltage is depleted (portion 703 of $V_{CAP}$ discharge line 702 of FIG. 7D and $V_{CAP}+V_{DIS}$ line 761 of FIG. 7E), voltage may be added ($V_{CAP}+V_{DIS}$ line 765 of FIG. 7E) to maintain a discharging voltage ($V_{CAP}+V_{DIS}$) sufficient to deliver the constant current active discharge current (e.g., discharging voltage magnitude greater than $V_I$).

Knowing the starting voltage associated with the charge stored by the capacitance and that this voltage depletes linearly when a constant current is used (see ideal voltage discharge line 701 of FIG. 7D), a second phase of the adaptive active discharge pulse (associated with discharge pulse voltage magnitude 752 of FIG. 7C and portion 704 of $V_{CAP}$ discharge line 702 of FIG. 7D) may be provided with a minimum voltage by anode source 640 which is calculated to facilitate the desired discharge current. In the example illustrated in FIG. 7C, the voltage provided in the second phase of the adaptive active discharge pulse has a voltage magnitude of 1 volt.

Again, as the stored voltage is depleted (portion 704 of $V_{CAP}$ discharge line 702 of FIG. 7D and $V_{CAP}+V_{DIS}$ line 762 of FIG. 7E), voltage may be added ($V_{CAP}+V_{DIS}$ line 766 of FIG. 7E) to maintain a discharging voltage ($V_{CAP}+V_{DIS}$) sufficient to deliver the constant current active discharge current (e.g., discharging voltage magnitude greater than $V_I$). Accordingly, a third phase of the adaptive active discharge pulse may be provided with an increased, minimum voltage by anode source 640 which is calculated to facilitate the desired discharge current. In the example illustrated in FIG. 7C, the voltage provided in the third phase of the adaptive active discharge pulse has a voltage magnitude of 2 volts.

According to the illustrated embodiment, substantially the remainder of the stored voltage is depleted (portion 705 of $V_{CAP}$ discharge line 702 of FIG. 7D and $V_{CAP}+V_{DIS}$ line 763 of FIG. 7E) during the third phase of the adaptive active discharge pulse. Accordingly, additional discharge voltage ($V_{DIS}$) is not added thereafter to maintain a discharging voltage ($V_{CAP}+V_{DIS}$) sufficient to deliver the constant current active discharge current (e.g., discharging voltage magnitude greater than $V_I$), but rather the adaptive active discharge pulse is concluded. It should be appreciated that passive discharge techniques may be implemented in combination with adaptive active discharge pulses, such as after the adaptive active discharge pulse has concluded as shown in FIG. 7F.

In addition to or in the alternative to calculating a voltage to be applied for facilitating the desired active discharge current based upon the linear depletion of the charge on the capacitance, some embodiments may operate to make measurements during active discharge to determine if an appropriate voltage is being applied. For example, a current error provided by feed back circuit 520, as described above, may be utilized during an active discharge pulse to determine that a voltage increase should be made with respect to anode source 640. Similarly, where the voltage provided by anode source 640 is in excess of that needed to facilitate delivery of a desired active discharge current, excess voltage will be present at node 502, as discussed above. Accordingly, the above current error and voltage information may be used in determining when to increment or decrement a voltage provided by anode source 640 during successive pulses or even during the pulse itself.

It should be appreciated that the embodiment of adaptive active discharge illustrated in FIGS. 7C-7F results in a discharging voltage ($V_{CAP}+V_{DIS}$) dropping below the voltage ($V_I$) needed to facilitate the desired discharge current ($I_{DIS}$), thereby resulting in voltage limiting of the discharge current (i.e., generating current errors) during brief times (see phases 771, 772, 773 of pulse 760 in FIG. 7F) in each of the illustrated discharge phases. Specifically, the magnitude of the discharging voltage ($V_{CAP}$+$V_{DIS}$) falls below voltage $V_I$ at the end of the first and second discharge phases as shown in FIG. 7E. Accordingly, the discharge current ($I_{DIS}$) shown in the illustrated embodiment is not the ideal constant current as shown in FIG. 7F. This deviation from constant current results in $V_{CAP}$ discharge line 702 deviating from ideal voltage discharge line 701 of FIG. 7D. Accordingly, a slight charge imbalance may result in a remaining voltage ($V_{REM}$) being present in the capacitance. However, as discussed above, a small amount of charge imbalance may remain without affecting the stimulation currents of subsequent pulses. Moreover, passive discharge techniques may be implemented, as shown in FIG. 7F, to reduce this charge imbalance. Accordingly, a voltage available from voltage multiplier 151 may be selected which is very near a desired discharge voltage, but which is insufficient to maintain a discharging voltage when summed with the voltage of the capacitance as the capacitance voltage is depleted, in order to optimize power consumption during adaptive active discharge.

Figure 8:
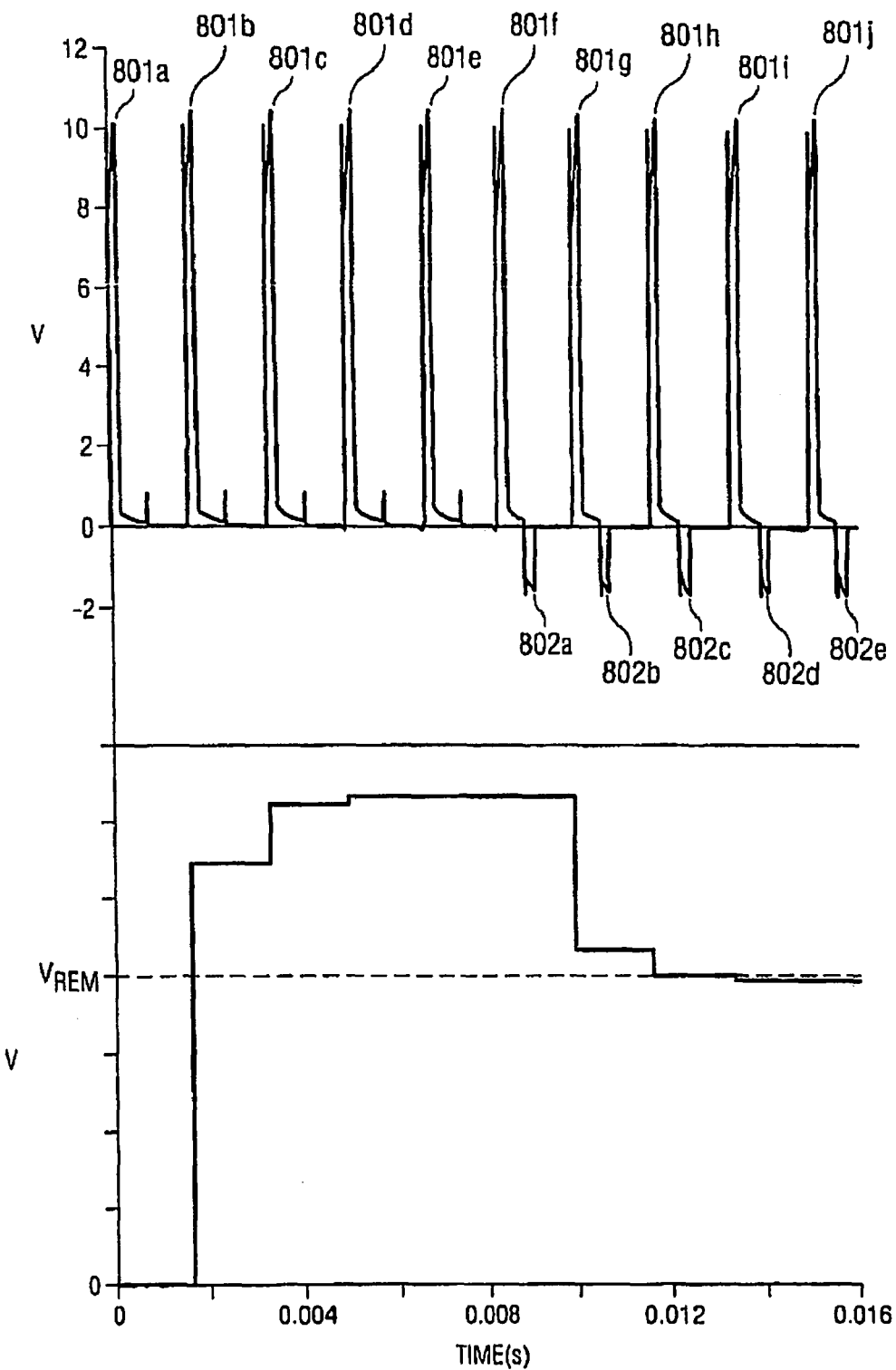
FIG. 8 shows diagrams of implementation of adaptive active discharge according to some embodiments.

Directing attention to FIG. 8, graphs showing the effects of implementation of adaptive active discharging as described above are shown. In the upper graph of FIG. 8, a series of stimulation pulses are shown as pulses 801a-801j. In the upper graph of FIG. 8, a plot of the voltage associated with the charge remaining on the capacitance is shown. It can be seen that when no active discharge pulse is provided (i.e., no active discharge between stimulation pulses 801a-801f), the voltage of the charge remaining on the capacitance rises to a steady state voltage. This steady state voltage is higher than a remaining charge voltage ($V_{REM}$) determined to be acceptable for delivery of a desired current in a subsequent stimulation pulse. Therefore, active discharge is implemented after stimulation pulse 801f according to some embodiments (it being appreciated that some embodiments may not wait until the voltage of the charge remaining on the capacitance to reach a steady state before implementing active discharge, but such is shown in FIG. 8 to illustrate the result if no active discharge is implemented). It can be seen that as active discharge pulses 802a-802e are applied, the voltage of the charge remaining on the capacitance begins to fall, reaching a steady state voltage. Application of adaptive active discharge pulses according to some embodiments operates to reduce the voltage of the charge remaining on the capacitance to a point just below the remaining charge voltage ($V_{REM}$) determined to be acceptable for delivery of a desired current in a subsequent stimulation pulse.

It should be appreciated that in the foregoing example, an active discharge pulse may not completely remove the charge from the capacitance. It has been discovered that some amount of charge may remain on the capacitance without resulting in charge accumulation which prevents delivery of desired currents. Accordingly, state machine 601 of a preferred embodiment optimizes adjustment of the active discharge pulses to provide sufficient discharge of the capacitance to avoid charge accumulation which may prevent delivery of a desired current with respect to a subsequent stimulation pulse, although perhaps leaving some charge remaining on the capacitance, and to minimize energy consumption associated with providing active discharge.

It should be appreciated that, although active discharge employing non-1:1 configurations provides substantial energy savings over techniques employing 1:1 active discharge, some embodiments employing adaptive active discharge techniques provide additional energy savings. For example, a 1:3 active discharge configuration may utilize 133% of the energy of stimulation without active discharge. However, implementing an adaptive active discharge pulse as shown in FIG. 7C may utilize only 111%, or less, of the energy of stimulation without active discharge.

Moreover, implementation of adaptive active discharging according to some embodiments facilitates the use of a voltage source (e.g., voltage multiplier 151) in providing active discharge without requiring substantial periods for recharging voltage multiplier prior to its use in delivering a stimulation pulse. For example, where only the primary (unstacked) capacitors within a fractional voltage converter such as that shown in the above referenced patent application entitled "EFFICIENT FRACTIONAL VOLTAGE CONVERTER" are used in one or more phases of an active discharge pulse, perhaps in combination with the voltage stored on the capacitance to be discharged, those capacitors may be charged during active discharging, thereby reducing the amount of recharge time required between delivery of the active discharge pulse and a subsequent stimulation pulse. Some embodiments implement a capacitive voltage multiplier, such as that shown and described in the above referenced patent application entitled "EFFICIENT FRACTIONAL VOLTAGE CONVERTER," which provides charging of capacitors associated with particular output voltages even when those voltages are being output. Accordingly, some embodiments operate to select such voltages, where possible, for use in providing adaptive active discharge, thereby reducing the amount of recharge time between delivery of the active discharge pulse and a subsequent stimulation pulse.

Although an exemplary embodiment of adaptive active discharge has been shown herein, it should be appreciated that adaptive active discharging is not limited to the particular configuration shown. For example, more or less than 3 phases may be implemented with respect to an adaptive active discharge pulse. Additionally, adaptive active discharge may be implemented even where a charge voltage stored on the capacitance is not great enough to itself facilitate an active discharge current (i.e., an active discharge voltage may be applied in a first phase of the adaptive active discharge pulse). Likewise, the voltage applied need not be changed in each phase of an adaptive active discharge pulse.

Pulse shaping as described above is not limited to application with respect to providing adaptive active discharging according to some embodiments. For example, circuitry utilized in providing pulse shaping for adaptive active discharge pulses may additionally be utilized in providing a stepped stimulation pulse. As an example, during the first 33% of the time during a stimulation pulse, the amplitude of the stimulation pulse voltage may be 25-60% of that needed to deliver the desired stimulation current. This voltage may be selected so as to be sufficient to begin the hyper polarization of the nerves so that when the full stimulation voltage is applied in the remaining 66% of the stimulation pulse effectiveness of the stimulation pulse is not compromised. In such a situation, much less current is delivered during a portion of the stimulation pulse (in the example given, the first third of the stimulation pulse) although the same therapy is delivered. Accordingly, pulse shaping as described herein may be utilized to conserve energy with respect to the stimulation pulse, the active discharge pulse, and combinations thereof. Moreover, the foregoing pulse shaping may be utilized in selectively stimulating different sized fibers (nerves) by charging cells for responding to the stimulation pulse.

FIGS. 11A-11C depict conventional constant current pulse generation and FIG. 12 depicts the variation of voltage during constant current pulse generation to enable more energy efficient operation of a pulse generator device according to one representative embodiment. FIG. 11A depicts graph 1101 for a stimulation pulse when a constant voltage level is selected for a constant current stimulation pulse. When a constant voltage level is selected for a constant current stimulation pulse, the voltage level is selected such that it exceeds the required voltage level to provide a constant current for the entire duration of the stimulation pulse.

However, the actual voltage required during a stimulation pulse to provide a constant current level varies. FIG. 11B depicts graph 1102 of the instantaneous voltage required to provide a constant current stimulation pulse. At the beginning of the pulse, the required voltage (iR) for the constant current is largely a result of the overall resistance between the anode(s) and electrode(s) including any internal and external resistance, where "i" represents the current level of the constant current pulse and "R" represents the overall resistance. The required voltage increases as charge is stored in the blocking capacitor(s) of the implantable pulse generator. The voltage at the end of the stimulation pulse equals iR+iPW/C, where PW further represents the pulse width of the stimulation pulse and C represents the capacitance of the blocking capacitors.

FIG. 11C depicts graph 1103 which shows the wasted energy involved in using a constant voltage level through a constant current stimulation pulse. The upper portion of graph 1103 shows the constant voltage level as previously shown in FIG. 11A. The instantaneous required voltage is shown underneath the constant voltage level as previously shown in graph 1102. The shaded area between the constant voltage and the instantaneous required voltage represents the wasted energy. The energy is wasted, because a variable resistance is utilized during the stimulation pulse to ensure that the excess voltage does not result in current beyond the selected constant current level.

FIG. 12 depicts graph 1201 of a voltage profile for a constant current stimulation pulse according to one representative embodiment. The stimulation pulse is segmented into multiple partitions. Distinct voltages 1202, 1203, and 1204 are selected for each partition. Each voltage 1202, 1203, and 1204 is preferably selected such that the voltage exceeds the instantaneous required voltage throughout the respective partition. The minimum voltage available from the voltage converter to achieve the desired constant current level is preferably selected for each respective partition. The partitions, as defined by the change in the utilized voltage level, preferably transition immediately before the instantaneous required voltage reaches the currently employed voltage level. The partitions and voltages can be determined using real-time feedback during the stimulation pulse. Alternatively, a voltage profile can be defined in memory of the implantable pulse generators such as table 1300 of FIG. 13 where voltage levels (V1-V4) for respective partitions are defined for various stimulation amplitude levels. In some embodiments, the voltage profiles defined in table 1300 can be varied upon operation of the device. That is, the voltages represented in table 1300 can be changed in an adaptive manner to optimize the energy consumption of pulse generation. Any suitable feedback mechanism can be employed for such adaptation.

In some embodiments, transitions between different voltages involve preferably a substantially square step between the different voltages, without spikes or substantial drops. Digitally controlled resistor 650 (FIG. 6A) is utilized according to some embodiments to provide desired waveforms. Specifically, digitally controlled resistor 650 of some embodiments implements a thermometer code architecture to facilitate control for selecting voltages as described above with respect to active discharge and stimulation pulse wave shaping.

In addition to the above described non-1:1 active discharge pulses, some embodiments provide cathodic first stimulation pulse configurations in which non-1:1 configurations are implemented. For example, some embodiments may implement 4:1, 3:1, and 2:1 cathodic first stimulation pulse configurations. Such cathodic first stimulation configurations may be used in selectively stimulating different sized fibers (nerves) by charging cells for responding to an anodic stimulation pulse. For example, particular electrodes of electrodes 132-135 used in providing a stimulation pulse may be disposed near various fibers, including the fibers to be stimulated and fibers other than the ones to be stimulated. These fibers may be of differing sizes. By applying a cathodic first stimulation pulse to charge cells of the fibers to be stimulated (such as where the fibers to be stimulated are larger than those which are not to be stimulated), delivery of a subsequent anodic stimulation pulse may stimulate the fibers for which stimulation is desired substantially without stimulating other fibers.

It should be appreciated that, although active discharge embodiments have been described above with reference to constant current systems, active discharge according to alternative embodiments could be applied in constant voltage systems.

Although the above described embodiments provide energy efficient active discharge techniques, passive discharge remains a more energy efficient solution to removing energy stored in the capacitance. Accordingly, some embodiments operate to make more effective use of passive discharge.

Directing attention to FIG. 9, a high level flow diagram of operation of an embodiment in determining when to invoke passive and active discharging techniques is shown. As discussed above, the illustrated embodiment implement logic to determine at block 901 when a passive discharging technique does not sufficiently remove the stored energy in the period between stimulation pulses in order to implement active discharging conservatively. Such determinations may be based upon stimulation pulse settings (e.g., magnitude and frequency lower than passive discharge thresholds for a passive discharge determination and magnitude and frequency higher than active discharge thresholds for an active discharge determination) and/or measurement of charge accumulation (e.g., measurement of voltage remaining on the capacitance). If it is determined at block 901 that a passive discharging technique will sufficiently remove charge from the capacitance, processing proceeds to block 902 wherein passive discharging is invoked for one or more subsequent stimulation pulses. However, it if is determined that a passive discharging technique will not sufficient remove charge from the capacitance, processing proceeds to block 903.

Figure 10A:
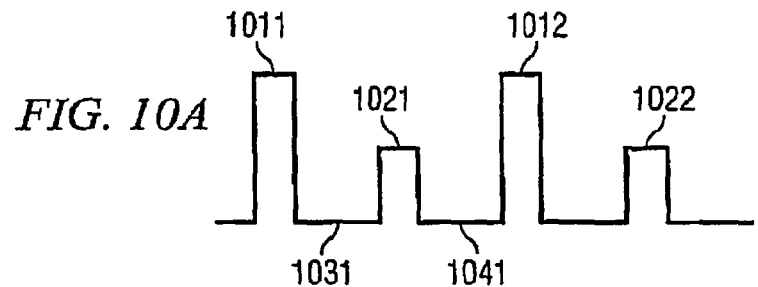
FIGS. 10A and 10B show a multi-stimulation set being altered to accommodate passive discharge techniques according to one embodiment.

At block 903 a determination is made with respect to whether a multi-stimulation set is being used. For example, two stimulation sets may be interleaved by IPG 110 to provide stimulation with respect to different areas of a body into which IPG 110 is implanted. Such interleaving may provide, for example, a stimulation pulse (e.g., stimulation pulse 1011 of FIG. 10A) associated with a first stimulation program, followed by a stimulation pulse (e.g., stimulation pulse 1021) associated with a second stimulation program, followed by a stimulation pulse (e.g., stimulation pulse 1012) associated with the first stimulation program, followed by a stimulation pulse (e.g., stimulation pulse 1022) associated with the second stimulation program, an so on. If it is determined at block 903 that a multi-stimulation set is not being used, processing proceeds to block 906 wherein appropriate active discharge settings are determined, as discussed below. However, if it is determined that a multi-stimulation set is being used, processing proceeds to block 904.

At block 904 a determination is made as to whether the stimulation pulse pattern of the multi-stimulation set can be adjusted to accommodate passive discharge. In particular, the embodiment illustrated in FIG. 9 operates to alter stimulation pulse patterns to make more effective use of passive discharge. Thus the determination made at block 904 according a preferred embodiment analyzes the stimulation pulse pattern of the multi-stimulation set to determine if the pulse pattern may be altered to accommodate passive discharge, or perhaps to minimize an amount of energy used in active discharge. If it is determined at block 904 that the stimulation pulse pattern cannot be adjusted to accommodate passive discharge, processing proceeds to block 906 wherein appropriate active discharge settings are determined, as discussed below. However, if it is determined that the stimulation pulse pattern can be adjusted to accommodate passive discharge, processing proceeds to block 905.

Figure 10B:
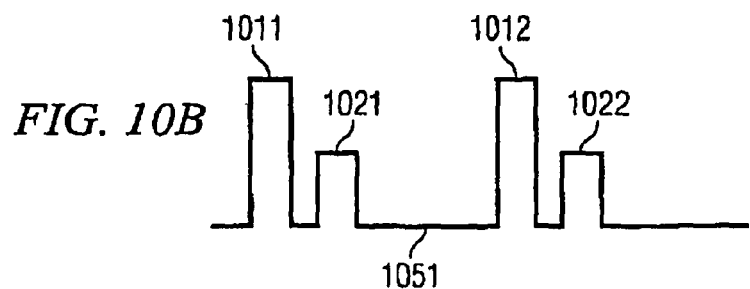

At block 905, a preferred embodiment implements a stimulation pattern to provide delayed passive discharge. Specifically, rather than deliver a first stimulation pulse (e.g., stimulation pulse 1011), followed by its corresponding discharge period (e.g., discharge period 1031), and deliver a second stimulation pulse (e.g., stimulation pulse 1021), followed by its corresponding discharge period (e.g., discharge period 1041), embodiments operate to deliver a first stimulation pulse (e.g., stimulation pulse 1011 of FIG. 10B) followed substantially immediately (e.g., accommodating delays associated with circuitry used in delivering the pulses) by a second stimulation pulse (e.g., stimulation pulse 1021 of FIG. 10B), with a passive discharge period (discharge period 1051) following the plurality of stimulation pulses. For example, where a multi-stimulation set is implemented (e.g., a first stimulation set uses a first set of electrodes to deliver a first stimulation pulse and a second stimulation set uses a second set of electrodes to deliver a second stimulation pulse) the frequency of delivery of successive stimulation pulses (assuming these stimulation pulses are equally spaced in time) may leave insufficient time for passive discharge to satisfactorily discharge the energy stored on the capacitance associated with either or both sets of electrodes. However, delayed passive discharge techniques of embodiments operate to consolidate the discharge periods (e.g., discharge periods 1031 and 1041 of FIG. 10A) into a longer discharge period (e.g., discharge period 1051 of FIG. 10B), allowing passive discharge to be used (albeit delayed with respect to one or more stimulation pulse) when active discharge techniques might otherwise be indicated. It should be appreciated that, although delayed passive discharge has been described above with reference to two stimulation pulses, some embodiments may implement delayed passive discharge with respect to two or more stimulation pulses.

After implementation of a stimulation pattern to provide delayed passive discharge at block 905, processing according to the illustrated embodiment proceeds to block 902. At block 902 passive discharging is invoked for one or more subsequent stimulation pulses. For example, the passive/active discharge determinations of FIG. 9 may be implemented with respect to each stimulation pulse. However, the passive/active discharge determinations of FIG. 9 may be implemented periodically, in response to a stimulation setting change or other event, etcetera.

At block 906, arrived at in the illustrated embodiment if passive discharging was not indicated and either no multi-stimulation sets are being used or the multi-stimulation sets being used cannot be adjusted to accommodate passive discharge, appropriate active discharge settings are determined. For example, the magnitude and duration of an active discharge pulse may be determined at block 906. Additionally, adaptive active discharge parameters (e.g., the number of discharge phases in an adaptive active discharge pulse, the magnitude and duration of adaptive active discharge pulse phases, etcetera) may be determined at block 906. Active discharge parameters implemented according to some embodiments may include multiple active discharge pulse settings, such as may be alternately or periodically implemented to provide time averaged charge accumulation dissipation. It should be appreciated that, although illustrated as determining active discharge settings, some embodiments may additionally determine passive discharge settings (e.g., whether to implement passive discharge following an active discharge pulse, whether the active discharge pulse may be optimized for use with passive discharge techniques, etcetera) at block 906.

After determining appropriate active discharge settings at block 906, processing according to the illustrated embodiment proceeds to block 907. At block 907 active discharging is invoked for one or more subsequent stimulation pulses. For example, the passive/active discharge determinations of FIG. 9 may be implemented with respect to each stimulation pulse. However, the passive/active discharge determinations of FIG. 9 may be implemented periodically, in response to a stimulation setting change or other event, etcetera.

Discharge techniques have been described above with reference to reducing the stored energy to a point which substantially removes the charge accumulation. However, as can be appreciated from the discussion above, some embodiments provide substantial control with respect to the amount of charge which is removed, and thus the amount of charge which remains after discharge. Some embodiments may operate to leave an amount of charge which affects the delivery of current in a subsequent stimulation pulse. For example, where a plurality of sets of electrodes are provided stimulation pulses in order to provide a field which creates a virtual electrode positioned differently than the actual electrodes, some embodiments may operate to provide different levels of discharge with respect to these sets of electrodes. Where the capacitance associated with different sets of electrodes is discharged to different levels, the current delivered in subsequent stimulation pulses may be affected differently. Accordingly, such an embodiment may be utilized to provide current steering with respect to the sets of electrodes, thus giving greater flexibility and control in the placement of a resulting virtual electrode, without requiring multiple current generators.

Pulse Ramping

Some embodiments implement pulse ramping when a significant change is made in the pulse amplitude. For example, pulse ramping may be used to provide a gradual start or ramped start when IPG 110 is activated to delivery stimulation pulses after having been in an off or idle state. Such pulse ramping may be linear or non-liner (e.g., parabolic, exponential, etcetera), or combinations thereof, according to some embodiments.

Although pulse ramping may be implemented by microcontroller 114 directly controlling the output provided by output driver 115, such as through incrementing voltages of voltage multiplier 151 by writing incremental voltage settings to voltage set 552 (FIG. 5), some embodiments operate to alleviate microcontroller 114 of much of the overhead associated with such pulse ramping control.

As described above, digitally controlled resistor 650 (FIG. 6A) is provided according to some embodiments in order to provide current scaling (as may be used in active discharge current ratio control), pulse shaping (as may be used in stimulation pulse and/or active discharge pulse wave shaping), etcetera. Some embodiments additionally or alternatively utilize digitally controlled resistor 650 to provide pulse ramping. For example, when a change in pulse amplitude is selected, microcontroller 114 may provide state machine 601 with a target amplitude and a number of steps to be implemented in transitioning to the target amplitude. The information regarding the number of steps for transitioning may include information regarding how those steps are to be taken (e.g., equal increments, large increments followed by decreasing increments, etcetera). Accordingly, state machine 601 may control digitally controlled resistor 650 to provide amplitude scaling to implement the steps desired in transitioning to the target amplitude. The use of thermometer code architecture with respect to digitally controlled resistor 650 facilitates the foregoing pulse ramping according to some embodiments.

Multi-Use ADC

As can be appreciated from the discussion above, some embodiments implement an analog-to-digital converter (ADC) which provides various functions, thereby utilizing little space in IPG 110 while providing robust functionality. For example, ADC 620 (FIG. 6A) provides measurement of a charge remaining upon the capacitance associated with load 501, indication of an error in the delivery of a desired current, indication of a higher than needed voltage for delivering a desired current, the remaining life/capacity of battery 121, and confirmation of an inverted electrode configuration as described above. Specifically, by selecting appropriate inputs to ADC 620 by multiplexer 610 in synchronization with particular operations of IPG 110 (e.g., during stimulation pulse delivery, after passive discharge, when the electrodes are coupled in an anode or cathode configuration, etcetera) the output of ADC 620 may be relied upon to provide the above described information. Moreover, some embodiments use ADC 620 to provide measurements in addition or in the alternative to those described above, such as measurement of battery voltage (e.g., measurement of the anode voltage when voltage multiplier 151 is set to provide $V_{BATT}$), the impedance of the load (e.g., measurement of anode to cathode voltage during a stimulation pulse for which the stimulation current is known), excess or adequate overhead voltage (e.g., measurement of a relatively large voltage drop across a transistor of feedback circuit 520), and/or the like.

In operation according to a preferred embodiment ADC 620 is time shared or multiplexed, perhaps with other circuitry of IPG 110, to provide multi-function use. For example, timing may be established with respect to delivery of stimulation pulses such that ADC 620 is controllably coupled to various circuit components and/or placed in particular operational modes during an appropriate period in the stimulation pulse cycle to accomplish a desired operation. For example, ADC 620 may be controlled to provide 1 bit operation at a point just prior to a stimulation pulse in order to make a comparison of a voltage remaining on the capacitance to a predetermined voltage (e.g., for charge accumulation determinations) and may be controlled to provide 8 bit operation during stimulation pulse generation to provide a measurement of a present battery voltage (e.g., for voltage multiplier control). Accordingly, timing control with respect to ADC 620 may be utilized to make mutually exclusive use of ADC 620 and/or other circuitry of IPG 110.

Operation of ADC 620 of a preferred embodiment comprises an auto trigger mode. For example, where it is known that particular measurements will be made every pulse, such as overhead voltage measurements, ADC 620 is configured to automatically trigger itself to make such measurements synchronous with the operation of IPG 110. However, various functions provided by ADC 620 may be controlled externally from ADC 620, such as under control of microcontroller 114. For example, where measurements are to be made less frequently, microcontroller 114 may provide a control signal to ADC 620 and/or multiplexer 610 to make such measurements when needed. Such external control of ADC 620 provides energy savings in that ADC 620 does not make unneeded measurements.

Although some specific embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the application that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of operating an implantable pulse generator for stimulating tissue of a patient, comprising:
providing power to a voltage converter of the implantable pulse generator at a first voltage level;
outputting a second voltage level by the voltage converter, the second voltage level being a variable voltage level that is controlled by a control signal provided to the voltage converter, the second voltage level being provided to pulse generating circuitry of the implantable pulse generator, the second voltage level being selectable from a plurality of voltages including non-integer multiples of the first voltage level;
generating pulses by the pulse generating circuitry, the pulse generating circuitry including current control circuitry for controlling the pulses to cause the pulses to provide constant current to tissue of the patient; and
applying at least two different control signals to the voltage converter during individual pulses to provide successively increasing voltages to the pulse generating circuitry during a respective pulse of constant current.

2. The method of claim 1 wherein the pulses are pulses that stimulate tissue of a patient.

3. The method of claim 1 wherein the pulses are pulses that discharge current stored on capacitors of the implantable pulse generator between stimulation pulses.

4. The method of claim 1 wherein the control signals are selected to provide a minimum voltage from a plurality of available voltages from the voltage converter that is necessary to provide the constant current during a respective segment of an individual pulse.

5. The method of claim 1 wherein the applying further comprises:
monitoring the pulse generating circuitry; and
changing the control signal provided to the voltage converter in response to the monitoring.

6. The method of claim 5 wherein the circuitry for monitoring signals control circuitry to change the control signal provided to the voltage converter immediately before the pulse generating circuitry is unable to provide the constant current at a current voltage level.

7. The method of claim 1 wherein the applying comprises:
changing the control signal provided to the voltage converter in response to a table of values stored in the implantable pulse generator, wherein each value in the table defines a voltage level for a specific partition of a plurality of partitions for a pulse at a respective amplitude level.

8. The method of claim 1 wherein the applying is controlled by a microprocessor or microcontroller.

9. The method of claim 1 wherein the applying is controlled by a control circuit without continuous control by a microprocessor or microcontroller.

10. The method of claim 1 wherein the applying provides control signals to a multiplexer that selects from a plurality of voltage levels provided by the voltage converter.

11. An implantable pulse generator for stimulating tissue of a patient, comprising:
a battery for powering the implantable pulse generator;
a voltage converter for providing a variable voltage level in response to a control signal, wherein the variable voltage level is selectable from a plurality of voltages including non-integer multiples of a supplied voltage level;
pulse generating circuitry for generating pulses, the pulse generating circuitry receiving a voltage output from the voltage converter, the pulse generating circuitry including current control circuitry for controlling the pulses to cause the pulses to provide constant current to tissue of the patient; and
a controller for controlling the voltage converter during operation of the pulse generating circuitry, wherein the controller causes at least two different control signals to be applied to the voltage converter during individual pulses to provide successively increasing voltages to the pulse generating circuitry during a respective pulse of constant current.

12. The implantable pulse generator of claim 11 wherein the controller comprises at least one item selected from the list consisting of a microcontroller, a microprocessor, and a control circuit.

13. The implantable pulse generator of claim 11 wherein the controller applies the at least two different control signals during generation of stimulation pulses.

14. The implantable pulse generator of claim 11 wherein the controller applies the at least two different control signals during generation of active discharge pulses.

15. The implantable pulse generator of claim 11 wherein the at least two different control signals are selected to provide a minimum voltage from a plurality of available voltages from the voltage converter that is necessary to provide the constant current during a respective segment of an individual pulse.

16. The implantable pulse generator of claim 11 wherein the controller comprises circuitry for monitoring a current level provided by the pulse generating circuitry.

17. The implantable pulse generator of claim 16 wherein the controller further comprises a comparator for comparing a voltage output from the voltage converter to a voltage output from the pulse generating circuitry.

18. The implantable pulse generator of claim 17 wherein the controller changes a control signal applied to the voltage converter when a voltage output from the voltage converter exceeds a voltage output from the pulse generating circuitry by a predetermined amount.

19. The implantable pulse generator of claim 11 further comprises:
a table of values stored in memory the implantable pulse generator, wherein each value in the table defines a voltage level for a specific partition of a plurality of partitions for a pulse at a respective amplitude level.

20. The implantable pulse generator of claim 11 wherein the voltage converter comprises a multiplexer that selects from a plurality of voltage levels provided by the voltage converter.

* * * * *